(12) United States Patent
Imran et al.

(10) Patent No.: US 10,507,313 B2
(45) Date of Patent: Dec. 17, 2019

(54) APPARATUS, SYSTEMS AND METHODS FOR DELIVERY OF MEDICATION TO THE BRAIN TO TREAT NEUROLOGICAL CONDITIONS

(71) Applicant: InCube Labs, LLC, San Jose, CA (US)

(72) Inventors: Mir Imran, Los Altos Hills, CA (US); Phillip Morgan, San Antonio, TX (US); Ben Tranchina, Boerne, TX (US); Paul Spehr, San Antonio, TX (US); Kyle Horlen, San Antonio, TX (US)

(73) Assignee: InCube Labs, LLC, San Jose, CA (US)

( * ) Notice: Subject to any disclaimer, the term of this patent is extended or adjusted under 35 U.S.C. 154(b) by 748 days.

(21) Appl. No.: 13/827,468

(22) Filed: Mar. 14, 2013

(65) Prior Publication Data
US 2013/0267928 A1   Oct. 10, 2013

Related U.S. Application Data

(60) Continuation-in-part of application No. 13/301,581, filed on Nov. 21, 2011, now Pat. No. 8,467,877,
(Continued)

(51) Int. Cl.
*A61M 37/00* (2006.01)
*A61M 5/142* (2006.01)
(Continued)

(52) U.S. Cl.
CPC .... *A61M 37/0069* (2013.01); *A61M 5/14276* (2013.01); *A61B 5/04004* (2013.01);
(Continued)

(58) Field of Classification Search
CPC ............ A61M 25/007; A61M 25/0138; A61M 25/0043; A61M 25/0067;
(Continued)

(56) References Cited

U.S. PATENT DOCUMENTS 3,885,561 A * 5/1975 Cami ................ A61M 25/007
137/493
4,829,070 A * 5/1989 Bodor .............. A61K 47/48161
514/307
(Continued)

FOREIGN PATENT DOCUMENTS

EP            0830876 A2    3/1998
JP         2009535155 A    10/2009
(Continued)

OTHER PUBLICATIONS

U.S. Appl. No. 13/681,825, filed Nov. 20, 2012, Imran et al.
(Continued)

*Primary Examiner* — Nathan R Price
*Assistant Examiner* — Justin L Zamory
(74) *Attorney, Agent, or Firm* — Wilson Sonsini Goodrich and Rosati, P.C.; Joel M. Harris

(57) ABSTRACT

Various embodiments provide an apparatus, system method for treating neurological conditions by delivering solid form medication to the ventricles or other areas of the brain. Particular embodiments provide an apparatus and method for treating epilepsy and other neurological conditions by delivering solid form medication to ventricles in the brain wherein the medication is contained in a diffusion chamber so as to allow the medication to dissolve in the cerebrospinal fluid of the brain and then diffuse out of the diffusion chamber to be delivered to the ventricles and brain tissue. In one or more embodiments, portions of apparatus have sufficient flexibility to conform to the shape of the ventricles of the brain when advanced into them and/or to not cause deformation of the ventricle sufficient to cause a significant physiologic effect.

41 Claims, 33 Drawing Sheets

Related U.S. Application Data which is a division of application No. 12/359,830, filed on Jan. 26, 2009, now Pat. No. 8,374,703, application No. 13/827,468, which is a continuation-in-part of application No. 13/681,825, filed on Nov. 20, 2012, now Pat. No. 9,107,993.

(60) Provisional application No. 61/629,609, filed on Nov. 21, 2011, provisional application No. 61/629,599, filed on Nov. 21, 2011.

(51) Int. Cl.

| A61B 5/04 | (2006.01) |
|---|---|
| A61B 5/0478 | (2006.01) |
| A61B 5/053 | (2006.01) |
| A61B 5/00 | (2006.01) |
| A61N 1/05 | (2006.01) |
| A61N 1/36 | (2006.01) |
| A61B 5/055 | (2006.01) |

(52) U.S. Cl.
CPC ............ *A61B 5/0478* (2013.01); *A61B 5/055* (2013.01); *A61B 5/0531* (2013.01); *A61B 5/4094* (2013.01); *A61B 5/4839* (2013.01); *A61N 1/0529* (2013.01); *A61N 1/0539* (2013.01); *A61N 1/36025* (2013.01); *A61N 1/36064* (2013.01); *A61N 1/36082* (2013.01)

(58) Field of Classification Search
CPC .... A61M 2025/0138; A61M 2025/006; A61M 2025/0057; A61M 2025/105; A61M 37/0069; A61M 31/007; A61M 2210/0693; A61M 2039/0276; A61M 2039/0294; A61N 1/36025; A61N 1/0539; A61B 5/4839; A61F 2/022
See application file for complete search history.

(56) References Cited

U.S. PATENT DOCUMENTS

| 4,950,232 | A | * | 8/1990 | Ruzicka | A61M 1/008 604/103.01 |
|---|---|---|---|---|---|
| 4,994,028 | A | * | 2/1991 | Leonard | A61M 37/0069 604/59 |
| 5,152,744 | A | * | 10/1992 | Krause | A61B 17/32002 604/22 |
| 5,170,785 | A | | 12/1992 | Heinz et al. | |
| 5,181,511 | A | | 1/1993 | Nickolls et al. | |
| 5,250,034 | A | * | 10/1993 | Appling | A61B 17/22 604/164.02 |
| 5,957,901 | A | * | 9/1999 | Mottola | A61M 25/007 604/264 |
| 5,978,702 | A | | 11/1999 | Ward | |
| 6,023,638 | A | | 2/2000 | Swanson | |
| 6,056,725 | A | * | 5/2000 | Elsberry | A61M 25/0068 604/151 |
| 6,227,203 | B1 | | 5/2001 | Rise | |
| 6,295,476 | B1 | | 9/2001 | Schaenzer | |
| 6,458,118 | B1 | | 10/2002 | Lent et al. | |
| 6,466,811 | B1 | | 10/2002 | Hassett | |
| 7,272,438 | B2 | | 9/2007 | Kroll et al. | |
| 7,308,310 | B1 | | 12/2007 | Levine et al. | |
| 9,107,993 | B2 | | 8/2015 | Imran et al. | |
| 2003/0045866 | A1 | * | 3/2003 | Petersen | A61M 25/0043 604/891.1 |
| 2003/0199956 | A1 | | 10/2003 | Struble et al. | |
| 2004/0019366 | A1 | | 1/2004 | Rottenberg et al. | |
| 2004/0215253 | A1 | | 10/2004 | Weinberg | |
| 2005/0090872 | A1 | | 4/2005 | Deno | |
| 2005/0137579 | A1 | * | 6/2005 | Heruth | A61M 5/14276 604/536 |
| 2005/0215991 | A1 | | 9/2005 | Altman et al. | |
| 2005/0288724 | A1 | | 12/2005 | Begemann et al. | |
| 2006/0149331 | A1 | | 7/2006 | Mann et al. | |
| 2006/0161211 | A1 | | 7/2006 | Thompson et al. | |
| 2006/0206157 | A1 | | 9/2006 | Hoijer | |
| 2007/0005004 | A1 | * | 1/2007 | Hynes | A61M 1/0084 604/43 |
| 2007/0239248 | A1 | | 10/2007 | Hastings et al. | |
| 2007/0275035 | A1 | | 11/2007 | Herman et al. | |
| 2008/0021505 | A1 | | 1/2008 | Hastings et al. | |
| 2008/0071338 | A1 | | 3/2008 | Jiang et al. | |
| 2008/0234773 | A1 | | 9/2008 | Ni et al. | |
| 2009/0131857 | A1 | | 5/2009 | Geiger | |
| 2009/0149833 | A1 | | 6/2009 | Cima et al. | |
| 2010/0114309 | A1 | | 5/2010 | De Juan, Jr. et al. | |
| 2010/0268291 | A1 | | 10/2010 | Imran | |
| 2010/0268295 | A1 | | 10/2010 | Imran | |
| 2010/0330149 | A1 | | 12/2010 | Daniel et al. | |
| 2012/0289816 | A1 | | 11/2012 | Mark et al. | |

FOREIGN PATENT DOCUMENTS

| WO | WO 97/24983 A2 | 7/1997 |
|---|---|---|
| WO | WO 2010/107507 A1 | 9/2010 |
| WO | WO 2011/106502 A2 | 9/2011 |
| WO | WO 2012/047931 A1 | 4/2012 |

OTHER PUBLICATIONS

European search report and opinion dated Sep. 11, 2012 for EP Application No. 10767635.5.
International search report and written opinion dated Mar. 4, 2013 for PCT/US2012/066156.
International search report and written opinion dated Nov. 29, 2010 for PCT/US2010/031748.
Office action dated May 25, 2011 for U.S. Appl. No. 12/427,733.
Office action dated Jun. 29, 2012 for U.S. Appl. No. 12/757,865.
Office action dated Jul. 12, 2012 for U.S. Appl. No. 12/427,733.
Office action dated Nov. 23, 2011 for U.S. Appl. No. 12/757,865.
European search report and search opinion dated Mar. 3, 2015 for EP Application No. 12852050.9.
Notice of allowance dated Apr. 17, 2015 for U.S. Appl. No. 13/681,825.
Office action dated Mar. 10, 2015 for U.S. Appl. No. 13/681,825.
Amano, Y. The cerebrospinal fluid production rate in the experimentally induced edematous brain and influences of dexamethasone upon it. Nagoya J Med Sci. Mar. 1969;31(3):427-41.
International search report and written opinion dated Dec. 5, 2014 for PCT/US2014/025018.
Office action dated May 22, 2014 for U.S. Appl. No. 13/681,825.
"European search report with written opinion dated Nov. 11, 2016 for EP14774821".
European search report with written opinion dated Jun. 28, 2017 for EP16193365.

* cited by examiner

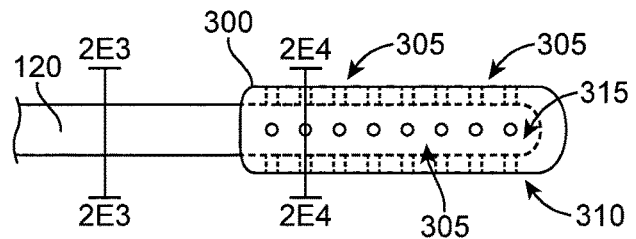
FIG. 2E1
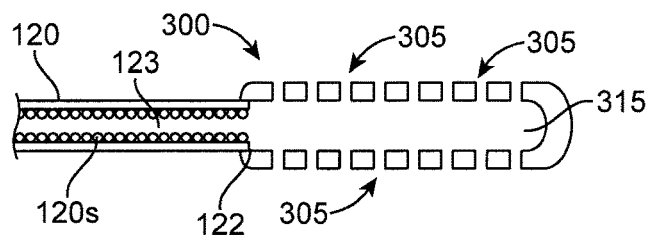
FIG. 2E2
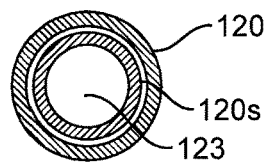
FIG. 2E3
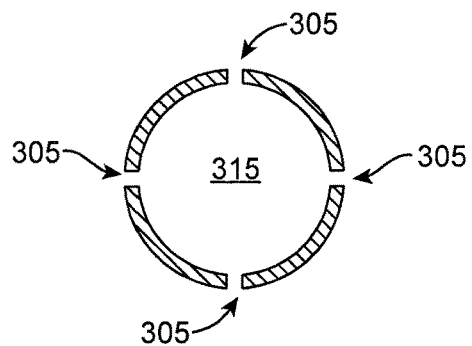
FIG. 2E4

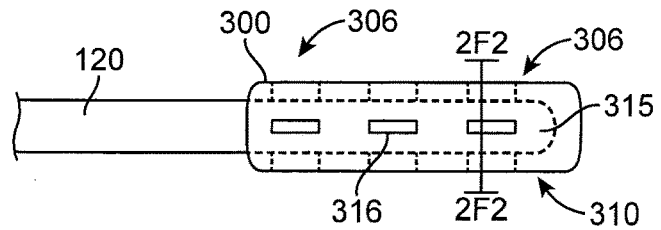
FIG. 2F1
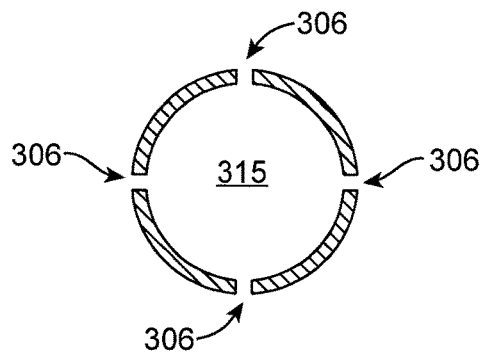
FIG. 2F2
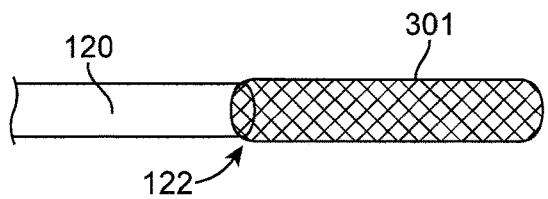
FIG. 2G1
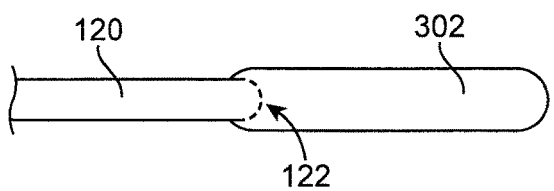
FIG. 2G2

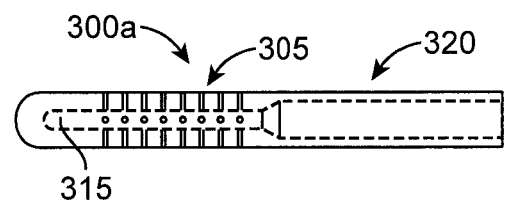
FIG. 2H1
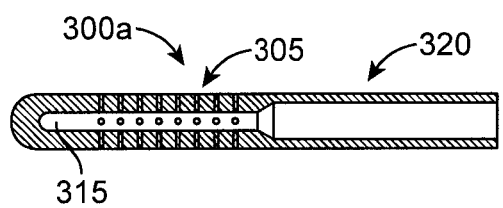
FIG. 2H2
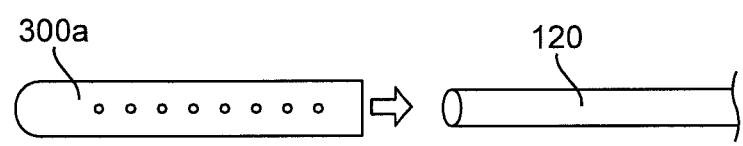
FIG. 2H3
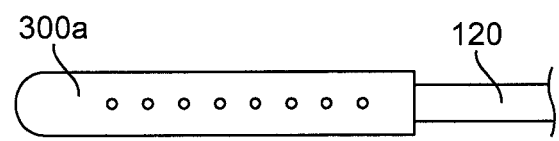
FIG. 2H4

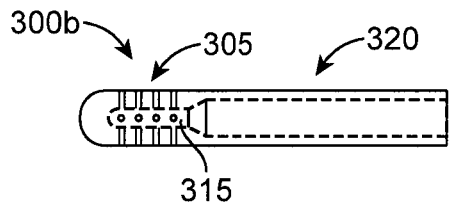
FIG. 2I1
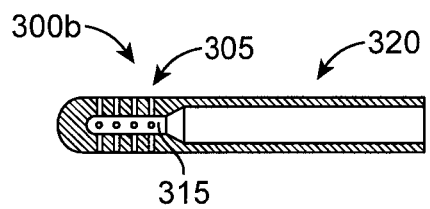
FIG. 2I2
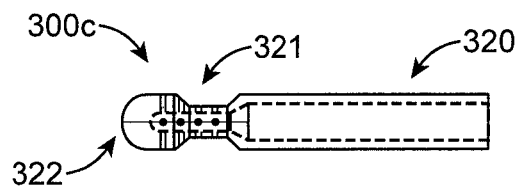
FIG. 2J1
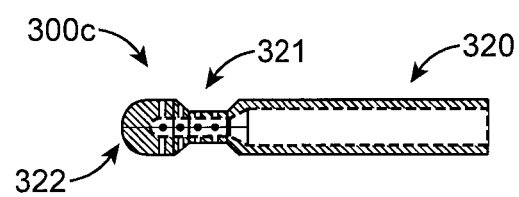
FIG. 2J2

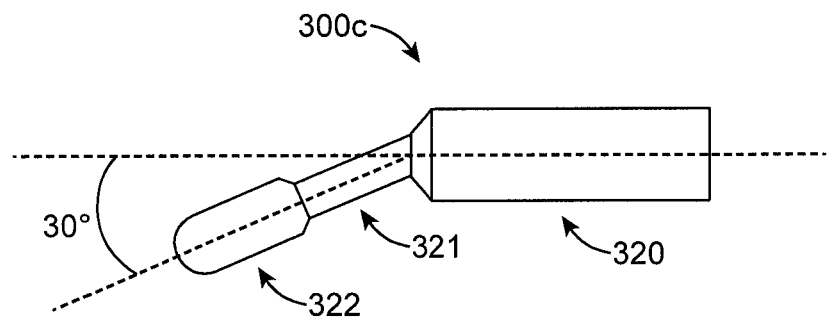
FIG. 2J3
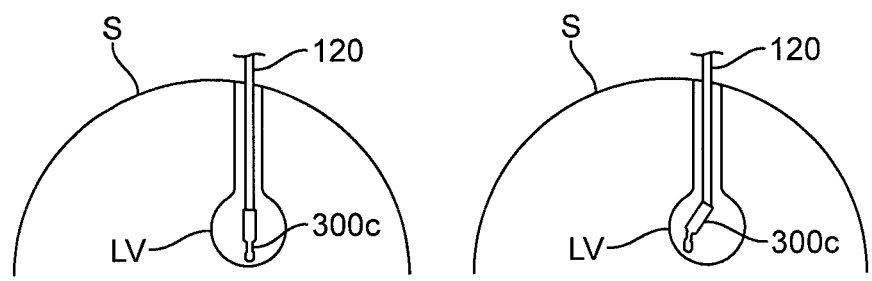
FIG. 2J4  FIG. 2J5
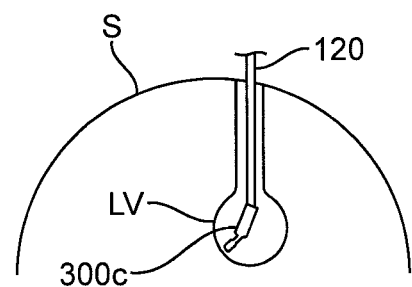
FIG. 2J6

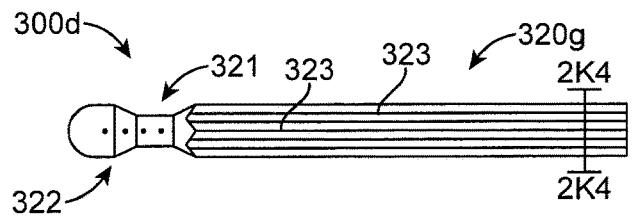
FIG. 2K1
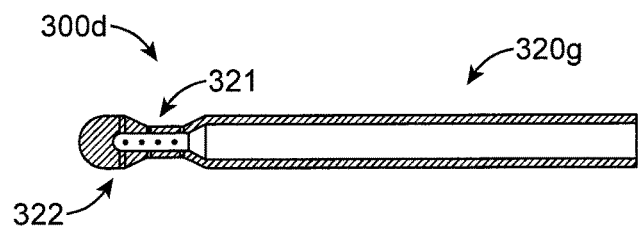
FIG. 2K2
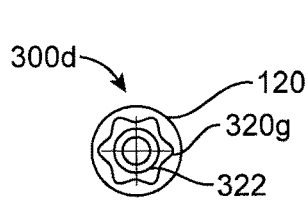
FIG. 2K3
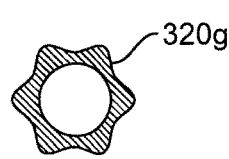
FIG. 2K4
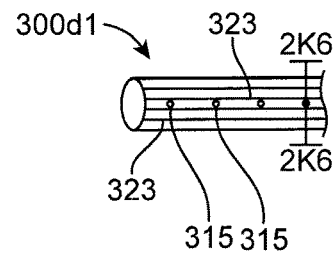
FIG. 2K5
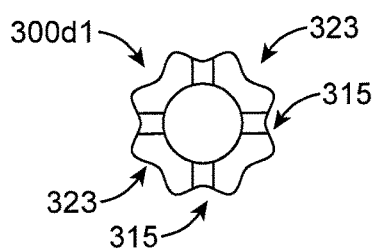
FIG. 2K6
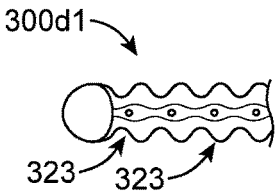
FIG. 2K7

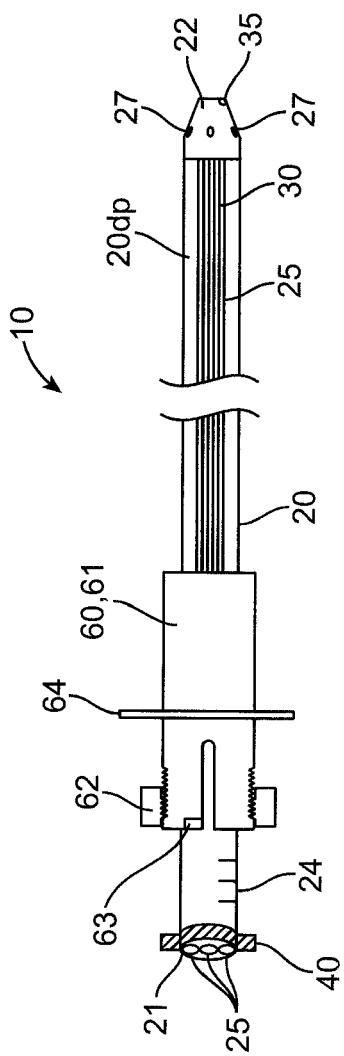
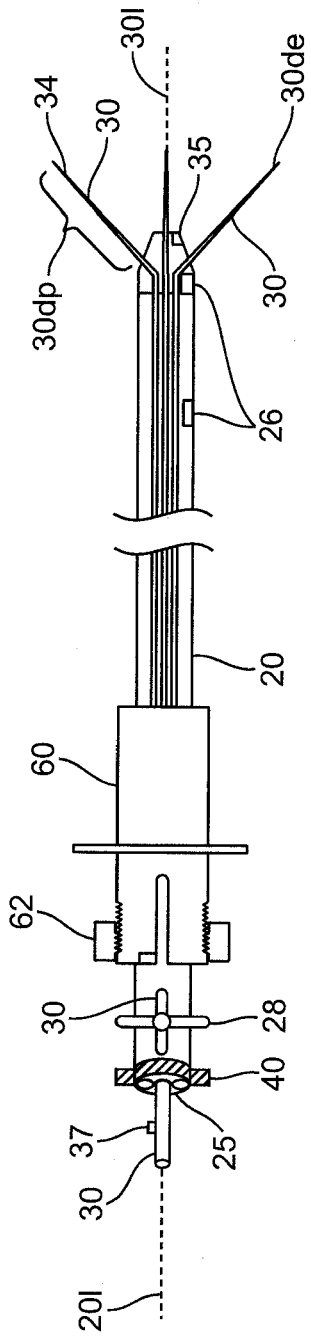

Normal Brain Activity

Brain Activity During a
Pre-Seizure or Seizure Event

APPARATUS, SYSTEMS AND METHODS FOR DELIVERY OF MEDICATION TO THE BRAIN TO TREAT NEUROLOGICAL CONDITIONS

RELATED APPLICATIONS

This application is a continuation-in-part of U.S. patent application Ser. No. 13/301,584, filed Nov. 21, 2011, now U.S. Pat. No. 8,467,877; which is a divisional of U.S. patent application Ser. No. 12/359,830, filed Jan. 26, 2009, now U.S. Pat. No. 8,374,703; and this application is also a continuation-in-part of U.S. application Ser. No. 13/681,825, filed Nov. 20, 2012, now U.S. Pat. No. 9,107,993; which claims the benefit of U.S. Provisional Application No. 61/629,599, filed Nov. 21, 2011; and claims the benefit of U.S. Provisional Application No. 61/629,609, filed Nov. 21, 2011; the disclosure of which are hereby incorporated by reference herein their entirety for all purposes.

FIELD OF THE INVENTION

Embodiments described herein relate to an apparatus, system and methods for the treatment of adverse neurological events or conditions. More specifically, embodiments described herein relate to an apparatus and methods for the treatment of neurological events or conditions by the delivery of solid form medication to the ventricles of the brain.

BACKGROUND OF THE INVENTION

There are a number of neurological events and conditions which are characterized by abnormal neural-electric activity in the brain including epilepsy, migraine headaches and even some forms of depression. Epilepsy is a disease characterized by recurrent unprovoked seizures which result in episodic impairment or loss of consciousness, abnormal motor phenomena, psychic or sensory disturbances, or the perturbation of the autonomic nervous system. It is caused by abnormal firing of neurons in the brain, a condition known as epileptogensis. These abnormal firings or electrical discharges may start in small neuronal populations (these are known as epileptogenci foci, the condition defined as focal epilepsy) or much larger areas of the brain (this condition is defined as generalized epilepsy). Often there can be a period of abnormal firing of neurons which precedes the full blown seizure. This period is known as a pre-seizure state and it can include one or more events of abnormal firing, known as pre-seizure events.

Whatever the cause, the human and financial impact of the disease is significant. The prevalence of epilepsy in the US is currently about three million, world-wide about fifty million, with 200,000 new cases diagnosed each year in the US alone. Ten percent of the American population will experience a seizure in their lifetime. Due to the impairing nature of epileptic seizures, the disease can prevent patients from performing a number of routine activities including driving car or operation of machinery. Many states put driving restrictions on those diagnosed with epilepsy. In a sub-population of patients, the severity of the disease is so extreme that they are essentially incapacitated. The economic cost of the disease is estimated to be $12.5 billion per year in direct and indirect costs.

While there are a number of available drug therapies for the treatment of epilepsy, these therapies have a number of side effects including hyperplasia, slurred speech and memory loss in large part due to the higher dose of drug which must be given systemically in order for the drug to reach the brain. They also require precise control of the therapeutic dosage to avoid occurrence of seizures for too low a dose or side effects for too high a dose. Thus, there is a need for improved methods for the treatment of neurological conditions such as epilepsy using drug therapy.

The current trend in many medical treatments requires the delivery of a drug to a specific target site so as to avoid the toxicity to other tissue and more precisely, as well controlling the timing and amount of drug delivered to that site. In many cases, this can require an implantable drug pump. However, due to their size and power requirements the current available pumps do not lend themselves to all medical applications, particularly for delivery of medication to the brain (e.g., for the treatment of various neurological conditions), where very precisely controlled doses of drug can be required. Also current devices can require frequent replenishment of the drug due to limited reservoir size and/or limited shelf life of the drug. Thus, there is a need for improved implantable drug delivery devices and associated methods for in vivo drug delivery of various neurological conditions.

BRIEF SUMMARY

Embodiments described herein provide a system apparatus and method for treating epilepsy and other neurological conditions such as migraine headaches and depression. Many embodiments provide an apparatus and method for treating epilepsy and other neurological conditions by delivering medication to the brain. Specific embodiments provide an apparatus and method for treating epilepsy and other neurological conditions by delivering solid form medication to the ventricle or other areas of the brain. Particular embodiments provide an apparatus and method for treating epilepsy and other neurological conditions by delivering solid form medication to ventricles in the brain wherein the medication is contained in a diffusion chamber to as to allow the medication to dissolve in the cerebrospinal fluid of the brain. In one or more embodiments, portions of apparatus (e.g., the distal portions) have sufficient flexibility to conform to the shape of the ventricles of the brain when advanced into them. Also, such portions may desirably have sufficient flexibility so as to not cause deformation of the surface of the ventricles sufficient to cause a significant physiological effect such as a decrease in CSF production, loss of consciousness, etc.

One embodiment provides an apparatus for delivery of medication to the ventricles or other area within the brain of a patient comprising a flexible delivery member and a diffusion chamber coupled to a distal end of the flexible delivery member. The proximal end of the delivery member may be coupled to a drug storage device for storing a plurality of solid form medication elements. The delivery member may include a lumen for advancement of one or more medication element through the delivery member. The delivery member may comprise a catheter or other flexible tubing known in the art (e.g., a hypotube) and for ease of discussion will now be referred to as a catheter but other forms of flexible tubing are equally applicable. The catheter may be configured to be advanced into a selected ventricle of the brain from a site outside the brain. Typically, it is configured to be introduced into the brain through an opening in the skull such as a burr hole which may be fitted with a burr-hole adaptor. The catheter may comprise any number of biocompatible polymers known in the art including for example silicone, polyurethane, PTFF, etc. In some embodiments, the catheter lumen may also include an inner lining of coiled wire to maintain the patency of the lumen when the catheter is put into a bent or deformed position, such as when it conforms to the shape of a ventricle. In use, the wire lining can allow a drug pellet or other medication element to be delivered to the diffusion chamber even when the catheter is deformed or bent.

In various embodiments, the distal tip of the catheter and/or the proximal portion of the diffusion chamber may include an elastic self-closing septum for preventing fluid intrusion into the inner lumen. The septum includes a slit which is configured to open when the drug pellet is advanced against the slit so as to allow passage of the drug pellet through the septum and then close to fluid ingress into the catheter lumen.

The diffusion chamber will typically be coupled to the distal end of the delivery member at a proximal end of the chamber. In one or more embodiments, the joint between the diffusion chamber and the catheter (e.g., the distal end of the catheter and the proximal end of the diffusion chamber) may have a necked portion to allow the diffusion chamber to bend and flex or otherwise deform to the shape of the ventricles or other structure within the brain as well as provide for other flexible properties described herein. The proximal end of the chamber may also include the septum valve described above for receiving the medication element and preventing the flow of CSF or other fluid proximally into the catheter. The chamber may be fabricated from any number of biocompatible polymers known in the art including silicone, polyurethane and PTFE and co-polymers thereof The diffusion chamber can have a wall and an interior volume for receiving the medication element and at least one diffusion section positioned in the wall allowing cerebrospinal fluid (CSF) to enter and exit the chamber. Other means for allowing CSF to enter and exit the diffusion chamber are also contemplated such as the use of various porous materials or use of a pump. Further, the diffusion chamber can be configured to i) retain a medication element received from the delivery member; ii) dissolve the medication element in fluid (e.g., CSF) within the interior volume to form a drug solution; and iii) diffuse drug from the drug solution through the at least one diffusion section to CSF within the selected ventricle of the brain.

The diffusion section may comprise one or more of apertures or slits, which may be arranged in various patterns around the diffusion chamber. For example, in one or more embodiments, the chamber can have two groups of apertures or slits (e.g., 8 to 16 each) which are offset about 180 degrees from each other with respect to a central axis of the chamber or four groups which are offset about 90 degrees from each other. The apertures can comprise circular shaped openings having a diameter in the range of about 0.1 to 0.5 mm. The slits may have a width in that range and a length in the range of about 0.25 to 5 mm. The size and distribution of the openings can be selected to allow CSF to seep/diffusion in or out of the chamber at a selected rate to in turn achieve a selected rate of disintegration of the drug pellet and/or rate of diffusion of drug from the diffusion chamber.

In other embodiments, the diffusion section may also comprise a permeable or semi-permeable membrane, for example polyimide, allowing passage of a selected drug, e.g., furosemide, out of the chamber. Other membrane materials are also considered such as a polyurethane based membrane. In one or more embodiments, having a membrane based diffusion section, the diffusion chamber may also include a release valve (also referred to herein as a burp valve), allowing any pressure buildup in the diffusion chamber (which may impede diffusion) to be released. In one or more embodiments, the release or burp valve may correspond to a slit in the diffusion chamber wall which is configured to open at selection pressure and then close again.

In still other embodiments the diffusion section or sections may comprise a combination of slits/apertures and a permeable membrane. In one particular embodiment, the slits or aperture are placed over the permeable membrane allowing for CSF flow over the membrane so to increase diffusion of the drug out of the membrane. Other embodiments may include multiple diffusion sections some comprising aperture or slits and other membranes. In use, such embodiments allowing for a varying rate of diffusion of drug out of the diffusion chamber.

In still other embodiments, the diffusion section may also comprise various porous materials. Such material can comprise any number of porous biomaterials such as various polymeric fiber materials such as polyethylene teraphalate (PET) or NYLON. In preferred embodiments of a porous diffusion section, the section may be fabricated from DACRON, such as a DACRON mesh, which can be either woven or knitted. The size and porosity of the porous material can be selected to allow CSF to seep/diffuse in or out of the chamber at a selected rate to in turn achieve a selected rate of disintegration of the drug pellet and/or rate of diffusion of drug from the diffusion chamber. According to one or more embodiments, the porous section can have a uniform porosity so as to wick in CSF and diffuse out drug solution uniformly from substantially the entire area of the diffusion section. According to other embodiments, the diffusion section of the diffusion chamber can be fabricated from porous materials having varying porosity so as preferentially wick in CSF and weep out drug solution from specific portion of the diffusion section. In another variation, the diffusion chamber can comprise a basket structure of wound metal wire or and/or polymer fibers, the winding configured to allow sufficient space for the CSF to weep in and drug solution to weep out.

According to one or more embodiments, all or portion of the diffusion chamber may include channels in the wall of the diffusion chamber including in the diffusion section so as to maintain diffusion of the drug and/or drug solution from the diffusion section when that section contacts or is otherwise in close proximity to the ventricle wall (e.g., which may block diffusion of the drug out of the diffusion chamber). The channels may correspond to slots, curved or square shaped channels. In preferred embodiments, the channels are oriented with respect to a longitudinal axis of the diffusion chamber, but also may have a radial orientation a well, other orientations and combinations of orientations are also contemplated. In one particular embodiment, the channels may correspond to convolutions in the walls of the diffusion chamber (preferably having longitudinal orientation). The convolution may have a sine wave or similar shape with the troughs in the sine wave corresponding to the channels.

According to some embodiments, the channels may extend proximally along all or a portion of the length of the catheter so as to have the drug solution/drug be transported proximally by diffusion of the drug and/or flow of the drug solution proximally in the channel to reach more superficial areas of the brain including surface areas of the brain such as the motor cortex. The channels may be treated with various coatings to promote or enhance flow through the channels (e.g., by capillary action) in a proximal direction along the catheter. In use, such channels can provide a means for delivering drug to not only to the CSF in the ventricles of the brain, but also to other selected areas of brain tissue. This dual site delivery provides the benefit of producing a centralized (e.g., to CSF in the ventricle) and more localized delivery of drug to treat one more neurological conditions such as epilepsy where it may be desirable to deliver to two or more sites in the brain.

The medication element comprises at least one drug for the treatment of a disease or condition, e.g., furosemide for the treatment of a neurological condition such as epilepsy. Typically, it comprises a pellet which is referred to herein as a drug pellet, though other shapes and configurations are also contemplated. The drug pellet is configured to dissolve in CSF (cerebrospinal spinal fluid) or other fluid in the diffusion chamber and then diffuse out into the CSF in the brain. The drug pellet may be transported through an inner lumen of the catheter or other like structure (e.g., a hypotube) by means of an advanceable stylet or advancement member that is advanced from the drug storage device by an electric motor or other advancement means. According to one or more embodiments, the stylet may comprise a metal wire or ribbon that is wound for example in a spool and then unwound by drive means such as electrically driven pinch rollers. The stylet will typically have a ball tip that is sized to push the drug pellet through drug delivery lumen and out the septum; however other shapes are also contemplated such as hot dog shape, or a concave shaped tip having a concavity sized to engage the diameter of the drug pellet. Also the stylet tip may be configured to sense contact with the drug pellet so as to be able to determine that the pellet is being advanced and that the pellet has been ejected. This can be accomplished by configuring the tip and/or the stylet to be capacitively coupled to the drug pellet so as to sense changes in capacitance when the tip makes and breaks contact with the drug pellet.

According to one or more embodiments, the catheter (or other flexible delivery member) and/or diffusion chamber are sufficiently flexible such that during advancement of the apparatus into the ventricles of the brain one or both of the catheter and the diffusion chamber conform to the shape of a selected ventricle. In particular embodiment, the flexibility of one or both of these elements can allow the diffusion chamber to deform up to 30 degrees or more when advanced against a ventricular surface. Various embodiments and approaches for achieving such flexibility can include the use of necked section joining the catheter and diffusion chamber, as well as the of various flexible polymers known in the medical device arts including for example, PEBAX and various elastomers such as silicones and polyurethanes and co-polymers thereof. Other embodiments may employ various super-elastic metals known in the art, such as NITINOL.

Further, in various embodiments, the flexibility can be configured such that the catheter and diffusion chamber deform sufficiently to be advanced through the ventricular anatomy of the brain to reach a selected ventricle. The selected ventricle can include any of the major ventricles off the brain including for example, the left and right ventricle (including their inferior and posterior horns), the third ventricle and the fourth ventricle. Also, during such advancement and positioning, the flexibility is of the catheter and diffusion chamber is desirably configured such that the apparatus does not deform a ventricular wall of the brain sufficiently to cause a significant physiological effect. That effect can include a decrease in the production of CSF or a neurological effect such as loss of loss of consciousness, pain or numbness, vomiting or change in heart or respiration rate. In particular embodiments the decrease in CSF production may correspond to a drop below about 21 ml/hour, more preferably a drop below below 20 ml/hour. CSF production can be measures using spinal tap procedures and/or using various medical imaging modalities.

In another aspect various embodiments of the invention provide a system for the delivery of medication to the ventricles or other area brain comprising one or embodiments of the apparatus for such delivery described herein and a drug storage device which may be coupled operatively or directly to the proximal end of the catheter or other delivery member. The drug storage device may be configured to store a plurality of drug pellets or other solid form medication elements. It may also include means for advancing a medication element from the drug storage device into the lumen of the delivery catheter and then into the interior of the diffusion chamber. The advancement means may include a drive source such as an electric motor and an advancement member (driven by the drive source) such as a stylet for advancing the drug pellet from the drug storage device to the diffusion chamber.

In many embodiments, the system includes or is coupled to a controller for controlling one or more aspects of the medication delivery process including for example actuation and control of the drive source and advancement member to deliver a medication pellet into the brain or other location. The controller may correspond to a microprocessor other logic device which can be programmed to include a delivery regimen wherein medication is delivered at regular intervals (e.g., once or twice a day, etc.) over an extended period. It can also be configured to receive a signal (e.g., wireless or otherwise) to initiate the delivery of medication or to change the delivery regimen (e.g., from once a day to twice a day). In this way, the patient or a medical care provider can control the delivery of medication in response to a specific event (e.g., an episode of arrhythmia) or longer term changes in the patient's condition or diagnosis.

In one or more embodiments, the controller can be coupled to or otherwise receive inputs from electrodes or others sensors position in the brain or other location within the patient's body so as to control delivery of medication to the patient's brain. For example, when the controller receives an input from the sensor indicative of the onset or occurrence of an epileptic or other seizure, it may initiate the delivery of one or more medication pellets to the brain or other target tissue site so as to treat the medical condition. Both the initial and subsequent inputs from the sensor can be used to titrate the delivery of medication pellets over an extended period until the condition is dissipated or otherwise treated. The controller can also receive inputs from other sensors configured to measure the tissue concentration of the delivered drug. These inputs can also be used to titrate the delivery of the medication to achieve a selected concentration of drug (e.g., in CSF, plasma, tissue, etc.). The drug sensors can be positioned on distal portions of the drug delivery device such as on the catheter or the outside of the diffusion chamber, as well as other sites in the body (e.g., a vein or artery), in order to develop a pharmacokinetic model of the distribution of the drug at multiple sites in the body. The apparatus can also include a sensor coupled to the controller which indicates when the medication pellets have been used up and/or exactly how many are left. The controller in turn can signal this data to an external communication device such as a cell phone, portable monitor or remote monitor (e.g., at the physician's office). In this way, the patient and/or medical care provider can take appropriate action before the apparatus runs out of drug pellets or other medication elements.

In many embodiments, the pellet (including the drug dose) is configured to disintegrate and be dissolved by CSF or tissue fluids which seep or otherwise enter into the diffusion chamber. In some embodiments the pellet is configured to dissolve slowly in the diffusion chamber so as to provide a long term release of drug into the brain, e.g., long term release of furosemide for the propholactic treatment of epilepsy or other like condition. In other embodiments, the pellet can be configured to rapidly disintegrate and be dissolved in the CSF to treat the onset or occurrence of an epileptic seizure. This can be achieved through the use of one or more super disintegrants as well as disintegrating enhancing features (e.g., pores, cracks or other intrusions) in or one the pellet. The particular selection of disintegrants can be matched to configuration of the diffusion chamber (e.g., aperture size and number) and/or CSF flow rate. Faster disintegrants can be used in chambers with fewer opening and or areas of the brain with slower CSF flow rates. It can also be achieved by treating the pellet prior or after delivery into the diffusion chamber with mechanical, electromagnetic, acoustical or other energy to weaken the pellet structure, create cracks and other structural defects for the ingress of fluids or initiate the breakup of the pellet into smaller pieces.

In various applications, embodiments of the invention can be used to deliver solid form drugs or other therapeutic agent to any location in the brain to treat any number of neurological other conditions.

In an exemplary embodiment of a method for using a system of the invention, the drug reservoir can be implanted at or near a selected delivery site such as the base of the skull. Implantation can be done using an open or minimally invasive procedure. Prior to implantation, the drug reservoir can be loaded with a selected number of pellets to provide for delivery of pellets to the delivery site over an extended period of time, e.g., years. Once implanted, the pellets can be stored in the apparatus for an extended period of years (e.g., 1, 2, 5 or longer) without degradation or deleterious effect to the pellets (e.g., loss of drug potentcy or therapeutic effectiveness). The system can deliver solid form medication to the delivery site at regular intervals (e.g., once an hour day, week, month, etc.) or in response to an input from a sensor. In the latter case, the input can be indicative of a particular medical condition or event such as the onset or occurrence of epileptic or other seizure. Embodiments of the controller described herein can be used to determine when to initiate delivery based on the sensor input and/or the time intervals for delivery for embodiments employing delivery at regular intervals. In either case, the controller can send a signal to the drug storage device. There it disintegrates/degrades and is dissolved in local tissue fluids to treat a local target tissue site (e.g., it dissolves in the CSF to treat the brain), or it is subsequently absorbed into the blood stream where it is carried to a remote target tissue site (e.g., the liver, heart, etc.) or both. Further pellets can be delivered based on input from a sensor providing physiologic data predictive of the medical condition (e.g., blood glucose) or another sensor that is configured to sense the local and/or plasma concentration of the drug. In some embodiments, pellet delivery can be controlled by sensing the state of disintegration of previously delivered pellets. For example, another pellet can be delivered when it has been determined that the previous pellet is in a particular state of disintegration (e.g., it has been completely or substantially disintegrated). This can be achieved by sending and receiving a signal from the pellet such as an optical, ultrasound or electrical signal. For example, for the use of optical signal reflectance measurements can be used to determine the state of disintegration. A particular disintegration state can be determined when the reflectance signal falls below a particular threshold. Similar approaches can be used for use of reflected ultrasound or impedance. The pellet can even include various echogenic, or optically opaque or other agents to enhance the reflected ultrasonic, optical or other signal. The pellet may also include various optical indicia having one or more of a pattern, size or shape configured to provide an indication of the state of disintegration of the pellet.

Prior to or after implantation, a burr hole can be made at the top of the skull and can be fitted with a burr hole adapter known in the art. The catheter or other flexible delivery member of the intracranial delivery apparatus can then be positioned under the scalp and the proximal end connected to a proximal fitting of the drug reservoir the distal end is advanced through the burr hole and/or burr hole adaptor for positioning in a selected ventricle or other location in the brain. After the catheter is advanced through the burr hole it is then advanced through brain tissue and into a selected ventricle of the brain so as to position the diffusion chamber within the ventricle. Advancement may done under the guidance of various medical imaging modalities including for example, ultrasound, flouroscopy or MRI. In one more embodiments, the catheter and/or diffusion chamber can include one or more echogenic, radio-opaque, magnetic-opaque, or other markers to assist in placement using such image guidance.

As described herein, the catheter and diffusion chamber desirably conform to the shape of ventricles during advancement as well when positioned in the selected ventricle so as not cause any significant physiologic and/or neurologic effect to the patient such as loss of consciousness, numbness, vomiting, or decrease in CSF production (other physiologic and neurologic effects are also contemplated). In specific embodiments, the catheter and diffusion chamber are so positioned so as not deform the ventricle wall more than about 3 mm, with larger and smaller amounts also contemplated. Also they can be so positioned so as to exert no more than about 20 mmHg of pressure on the ventricle, more preferably no more than about 15 mmHg of pressure. In various embodiment, this can be achieved by configured the catheter and diffusion chamber to have sufficient flexibility to deform before this amount of pressure is reached. According to one more or more embodiments, this can be achieved by fabricating the catheter and diffusion chamber from not only flexible material but materials which soften upon exposure to CSF such as various hydrogel materials known in the art.

Once positioned in the ventricle or other location in the brain, CSF then enters into the diffusion chamber e.g., by wicking, capillary action, diffusion or other transport phenomenon. A sufficient period of time can be allowed for this to occur before drug delivery begins and/or the diffusion chamber can be pre-filled with the patient's own CSF. A drug pellet or other solid form drug element can then be advanced from the drug reservoir (or other drug storage device into) through the delivery catheter into the diffusion chamber. There is dissolves in the CSF in the diffusion chamber to form a drug solution. The drug then diffuses out of the chamber into CSF in the selected ventricle of the brain to provide a therapeutically effective dose of a drug for the treatment or prevention of a condition such as epilepsy. Depending the dose and other factors (e.g., the configuration of the diffusion chamber such as the size, number and position of apertures in the diffusion sections), it may also be configured to diffuse to other ventricles of the brain so to provide the therapeutically effective dose to those areas of the brain. For embodiments, of the delivery apparatus having channels running along the length of the catheter (as is described herein) the drug may then diffuse or flow in the drug solution (e.g., by capillary action) proximally along those channels to reach other areas of the brain including for example surface areas of the brain such as the motor cortex. Amount and rate of such diffusion can be controlled by selection of the length and depth of the channels. The channels may also be treated with coating to result in greater amounts of flow (by capillary action).

Further details of these and other embodiments and aspects of the invention are described more fully below, with reference to the attached drawing figures.

BRIEF DESCRIPTION OF THE DRAWINGS

FIG. 2e1 is a side view illustrating an embodiment of a drug delivery device which may be used in the embodiment of FIG. 2c.

FIG. 2e2 is a cutaway side view of the drug delivery device of FIG. 2e1.

FIG. 2e3 is a sectional view of the drug delivery device of FIG. 2e1 taken across line 2e3 in FIG. 2e1.

FIG. 2e4 is a sectional view of the drug delivery device of FIG. 2e1 taken across line 2e4 in FIG. 2e1.

FIG. 2f1 is a side view illustrating another embodiment of a drug delivery device which may be used in the embodiment of FIG. 2c.

FIG. 2f2 is a sectional view of the drug delivery device of FIG. 2f1 taken across line 2f2 in FIG. 2f1.

FIG. 2g1 is a side view of another embodiment of a drug delivery device which may be used in the embodiment of FIG. 2c.

FIG. 2g2 is a side view of another embodiment of a drug delivery device which may be used in the embodiment of FIG. 2c.

FIGS. 2h1, 2h2 show a side view and a cutaway side view, respectively, of another embodiment of a drug delivery device which may be used in the embodiment of FIG. 2c; FIGS. 2h3, 2h4 show side views of the drug delivery device of FIGS. 2h1, 2h2 being assembled together.

FIGS. 2i1, 2i2 show a side view and a cutaway side view, respectively, of another embodiment of a drug delivery device which may be used in the embodiment of FIG. 2c.

FIGS. 2j1, 2j2 show a side view and a cutaway side view, respectively, of another embodiment of a drug delivery device which may be used in the embodiment of FIG. 2c; FIG. 2j3 show a side view of the drug delivery device of FIGS. 2j1, 2j2 being bent; FIGS. 2j4, 2j5, and 2j6 show the drug delivery device of FIGS. 2j1-2j3 being inserted into the lateral ventricle of a patient.

FIGS. 2k1, 2k2, and 2k3 show a side view, a cutaway side view, and a front view, respectively, of another embodiment of a drug delivery device which may be used in the embodiment of FIG. 2c; FIG. 2k4 shows a sectional view of the drug delivery device of FIGS. 2k1, 2k2, and 2k3 taken across line 2k4 in FIG. 2k1.

FIG. 2k5 shows a side view of the distal-most end of another embodiment of a drug delivery device which may be used in the embodiment of FIG. 2c; FIG. 2k6 shows a sectional view of the drug delivery device of FIG. 2k5 taken across line 2k6 in FIG. 2k5.

FIG. 2k7 shows a side view of the distal-most end of another embodiment of a drug delivery device which may be used in the embodiment of FIG. 2c.

FIG. 3 is cut away side view of a distal portion of the deployed electrode members illustrating use of bent lumens in the introducer to deflect electrode members.

FIGS. 4a-4b are perspective views and FIG. 4c is a frontal cross-sectional view.

FIG. 5 is a perspective view showing the electrode members existing from the deflector.

FIG. 6a is side view showing an embodiment of the ANEA detection apparatus with the electrode members in the non deployed state inside the introducer.

FIG. 6b is side view showing an embodiment of the ANEA detection apparatus with the electrode members in advanced out of the introducer in a deployed state.

FIG. 8a shows an embodiment of an electrode having an abrupt bend, FIG. 8b shows an embodiment having a curved bend.

FIG. 10a illustrates an electrode member having a solid conductive core, while FIG. 10b illustrates an electrode member having at least one lumen.

FIG. 16a shows the burr hole opening in the skull. FIG. 16b shows placement of a burr hole plug in the burr hole opening. FIG. 16c shows the introduction and advancement of the introducer through the burr hole plug. FIG. 16d shows the full advancement of the introducer. FIG. 16e shows the deployment of the electrode members to a configuration for detecting the Foci.

FIG. 17a is over a period of normal activity and FIG. 17b is over a period of aberrant neural-electric activity in the brain.

DETAILED DESCRIPTION OF THE INVENTION

Figure 4A:
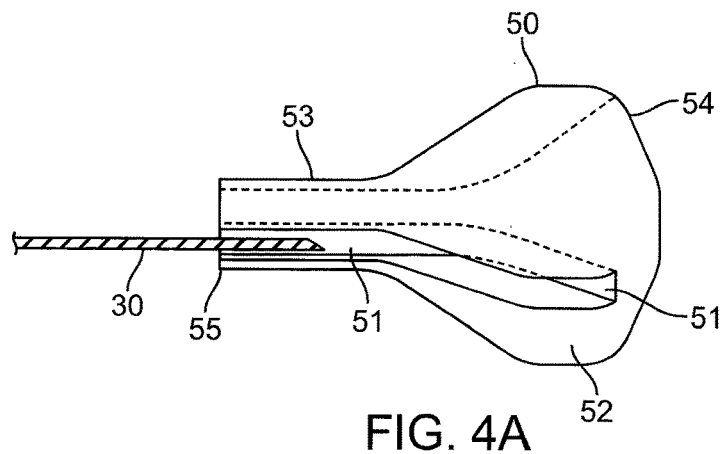
FIGS. 4a-4c are various views showing embodiments of a deflection fixture positioned within the introducer to deflect the electrode members.
Figure 4B:
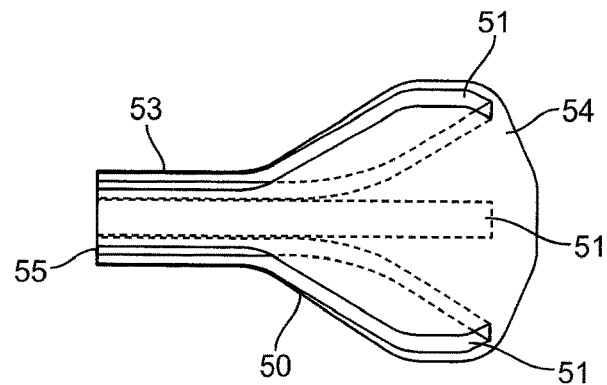
Figure 4C:
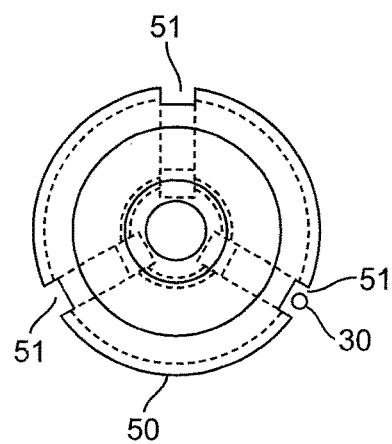

Various embodiments described herein provide a system, apparatus and method for detecting and treating various neurological events or conditions such as epilepsy, migraine headaches, depression, and various non-epileptic seizures. Many embodiments provide an apparatus and method for detecting aberrant activity such as aberrant neurological activity and/or cortical spreading depression (C SD) prior to the actual physical manifestation of the event or condition caused by the aberrant activity (e.g. detect the electrical activity and/or CSD prior to occurrence of an epileptic seizure, migraine or other neurological event or condition) and then use that information to initiate the delivery of a drug to prevent or reduce the duration of the seizure or other neurological event. Specific embodiments provide an apparatus and method for treating epilepsy and other neurological conditions by delivering solid form medication to the ventricle(s) or other areas of the brain. Particular embodiments provide an apparatus and method for treating epilepsy and other neurological conditions by delivering solid form medication to ventricles in the brain wherein the medication is contained in a diffusion chamber to as to allow the medication to dissolve in the cerebrospinal fluid of the brain. Diffusion chambers according to various embodiments are shown in FIGS. 2e1 to 2l, which show diffusion chambers 300 (FIGS. 2e1-2ef2), 301 (FIG. 2g1), 302 (FIG. 2g2), 300a (FIGS. 2h1-2h4), 300b (FIGS. 2i1, 2i2), 300c (FIG. 2j1-2j6), 300d (FIGS. 2k1-2k4), 300d1 (FIGS. 2k5-2k7), and 300e (FIG. 2l). In one or more embodiments, portions of the apparatus (e.g., the distal portions including the diffusion chamber) have sufficient flexibility to conform to the shape of the ventricles of the brain when advanced into them. Also, such portions desirably have sufficient flexibility so as to not cause deformation of the surface of the ventricles sufficient to cause a significant physiological effect such as a decrease in CSF production, loss of consciousness, vomiting, numbness, etc.

Also, many embodiments provide an apparatus system and method for the intracranial delivery of one or more drugs to various regions within the brain. Such drugs may be so delivered to prevent or reduce the duration of an epileptic seizure, migraine headache or other neurological condition by preventing, slowing or reducing the duration of aberrant neurological activity and/or a wave of cortical spreading depression.

In an embodiment, an apparatus is implanted at least partially in the brain that includes suitably oriented electrode members that are configured to be able to detect and locate the direction of aberrant neural-electric activity in the brain. Specific embodiments can detect and interpret an electric field generated by a foci or other origin of aberrant neural-electric activity. In an embodiment, such information is determined and interpreted as a marker to the onset of an epileptic seizure or other neurological event or condition.

In one or more embodiments, the marker of the onset of an epileptic seizure or other neurological event or condition can be used to control the delivery of a therapeutically amount of a drug such as an ion co-transporter antagonist to block, slow or reduce the duration of the aberrant neuro-electric activity and/or the duration a wave of cortical spreading depression so as to prevent or reduce the duration of the seizure. In one more embodiments the ion co-transporter antagonist may correspond to a cation-chloride co-transporter antagonist. Still more specifically, the cation-chloride co-transporter antagonist may correspond to a loop diuretic such as furosemide and/or its analogues and derivatives.

Still further, embodiments described herein provide for detection of aberrant neural-electric activity (ANEA) in a brain of a patient that is likely to cause an epileptic pre-seizure event or a seizure event. In an embodiment, an electric field that is caused or otherwise associated by the ANEA is detected from inside the brain or skull of the patient. An electric field vector characteristic is determined from the electric field. The electric vector is interpreted as being a marker to epileptic pre-seizure event or seizure event. The marker may correspond to a characteristic that is likely to be a precursor to the seizure. According to one or more embodiments, detecting the electrical field may be in form of detecting voltage (or current) on electrodes that are in the skull or brain at the time of ANEA. The marker may be then used to deliver a therapeutically effective dose of a drug.

Figure 1:
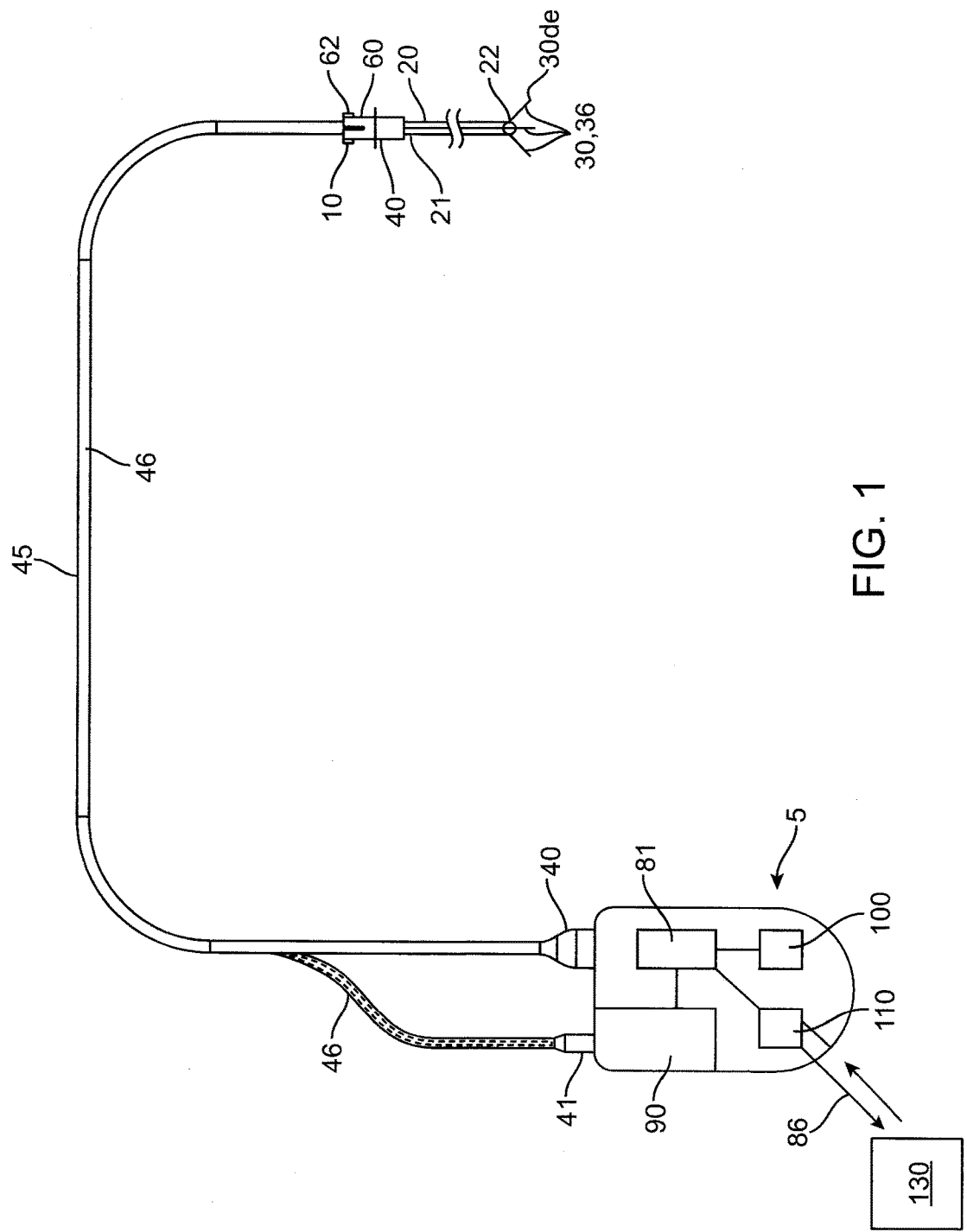
FIG. 1 is a plan view of an embodiment of a system and apparatus for detection of aberrant neural-electric activity (ANEA).
Figure 2A:
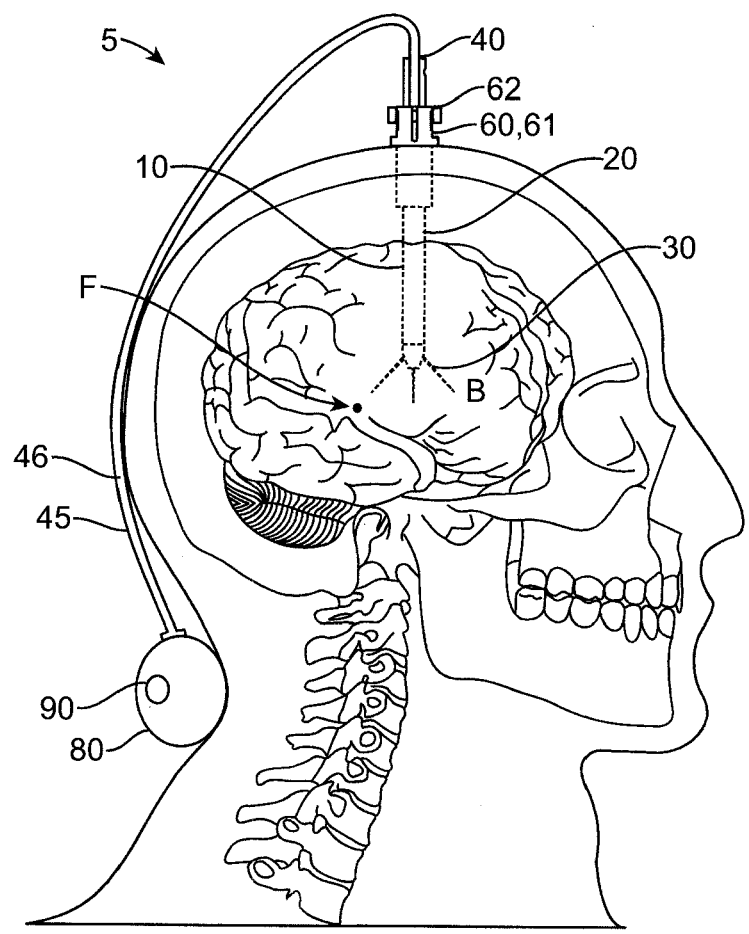
FIG. 2a is a side view showing placement and use of the system and apparatus from the embodiment of FIG. 1 to detect aberrant neural-electric activity in the brain.
Figure 2B:
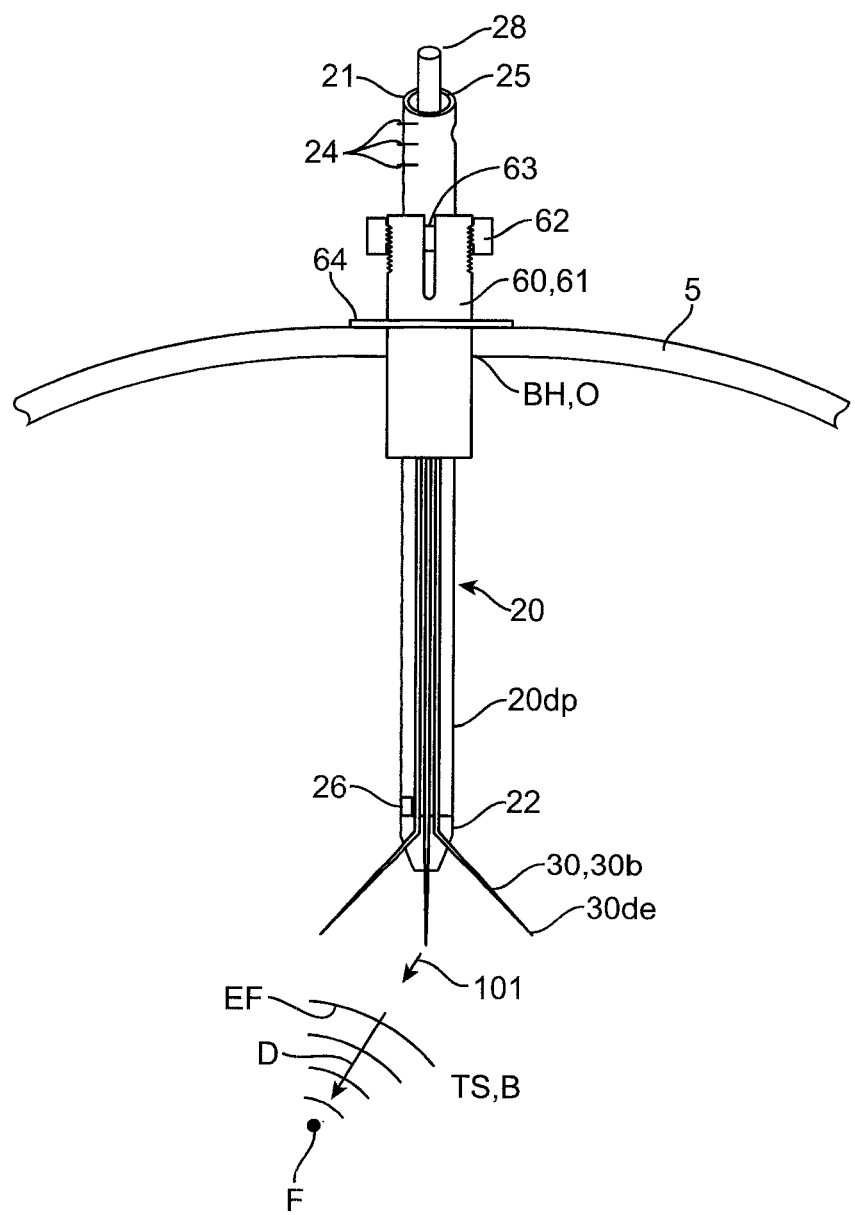
FIG. 2b is a side view showing placement of the plug in burr hole in the skull and the introduction of the ANEA detection apparatus at tissue site in the brain.
Figure 2C:
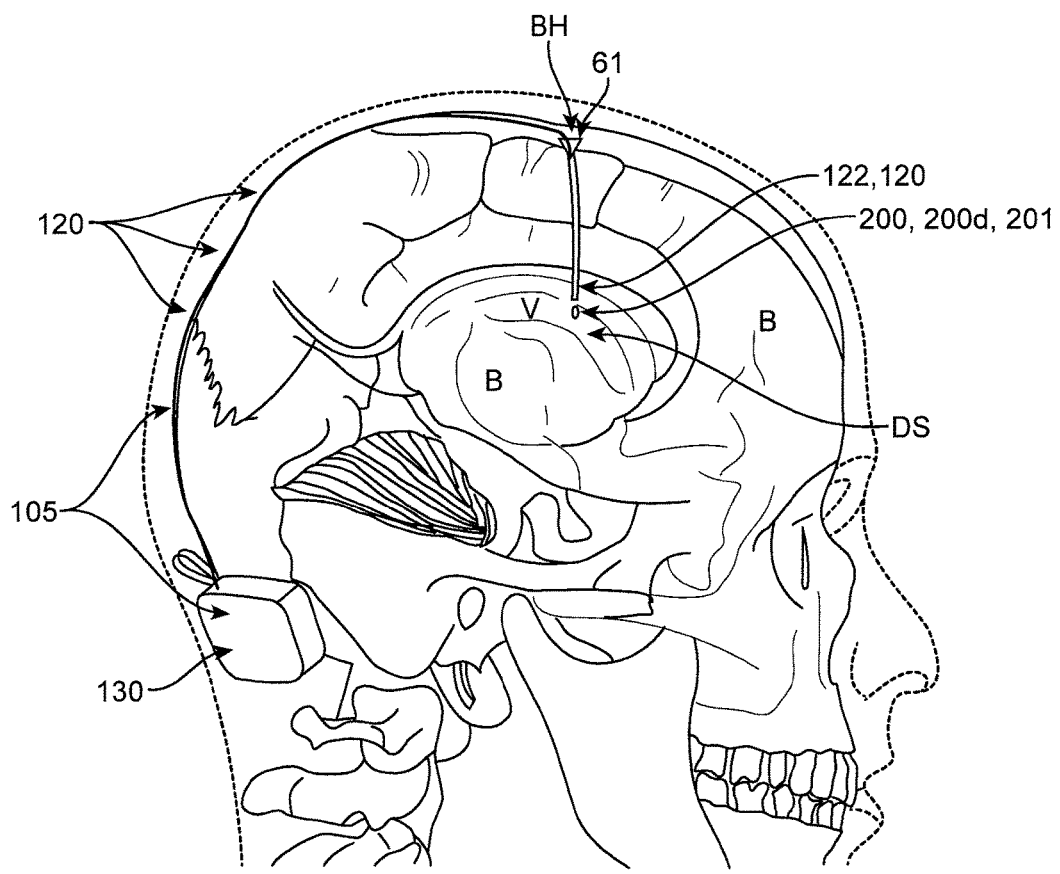
FIG. 2c is a side view illustrating an embodiment of a system for the intracranial delivery of a drug other therapeutic agent to the patient's brain.
Figure 2D:
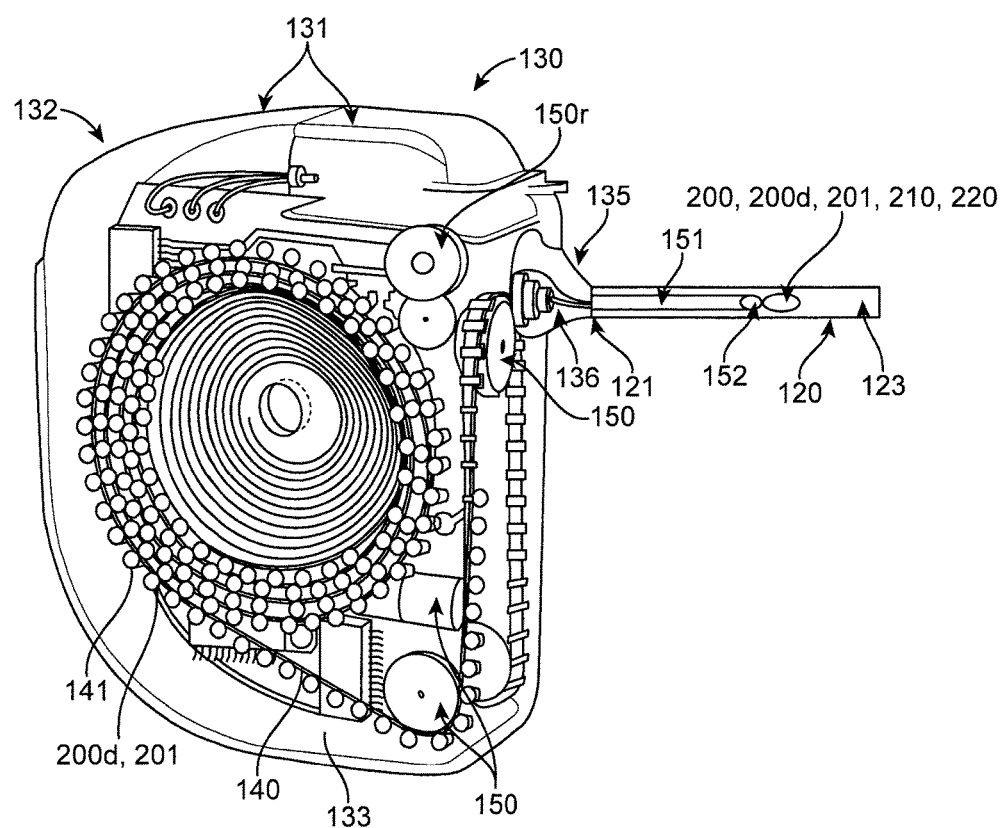
FIG. 2d is a side view illustrating an embodiment of a drug storage and delivery device which may be used in the embodiment of FIG. 2c.
Figure 2L:
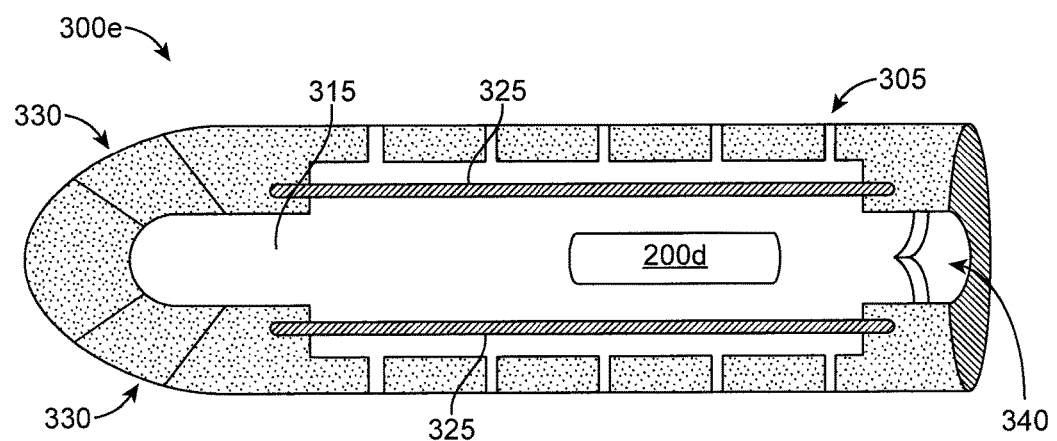
FIG. 2l is a cut away side view of another embodiment of a drug delivery device which may be used in the embodiment of FIG. 2c.
Figure 3:
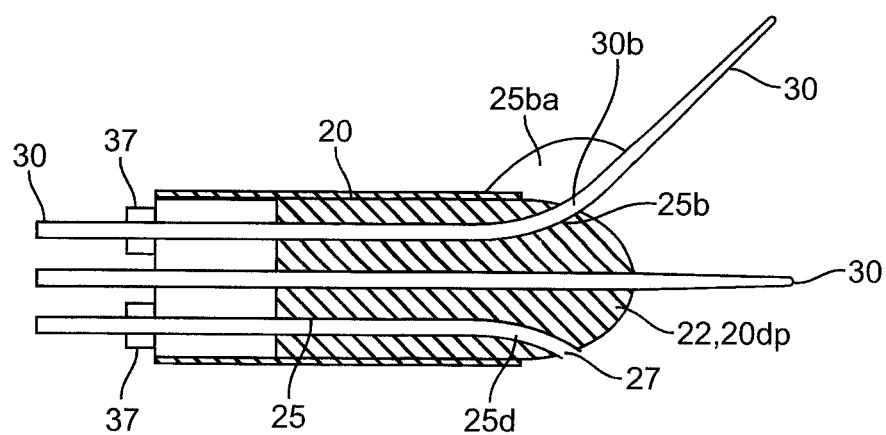

Referring now to FIGS. 1-3, various embodiments of the invention provide for a system 5 and apparatus 10 for detection of aberrant neural-electric activity (ANEA) and/or cortical spreading depression. System 5 comprises apparatus 10 and a control module 80 described herein. Apparatus 10 includes an introducer 20 having one or more lumens 25, a reference electrode 35 and a plurality of electrode members 30 which are advanceable in lumens 25 to be deployed into brain tissue. Electrode members 30 have a non-deployed state when positioned in the introducer and a deployed state when advanced out of the introducer. In the deployed state, the electrode members can have a bent shape 30B. This bent shape can be used to define a detection volume DV for detection of a Foci F of ANEA.

Introducer 20 has proximal and distal ends 21 and 22 and is configured to be inserted into the skull S of a patient so as to position the electrode members 30 at a target tissue site TS in the brain B. Proximal end 21 can be configured to be coupled to one or more electrical, fluidic or other connectors 40. Embodiments of electrical connectors 40 can include standard connectors such as USB and Firewire connectors and can be configured to be coupled to external processors, A/D converters and like circuitry. Connectors 40 can also comprise a communication port such as an RF or infrared port. In many embodiments, connector 40 is configured to be coupled to external control module 80. In these and related embodiments, connector 40 can be coupled to module 80 via a connecting member 45 which can include electrical wiring and one or more lumens 46 for delivery of fluids including drug containing fluids as well as solid. In one or more embodiments, member 45 may correspond to a catheter, such as a type used for CSF shunts and may be configured to be implanted subcutaneously under the patient's scalp.

In various embodiments, introducer 20 can be configured to be directly introduced into brain tissue through an opening O in the skull S, or it can be introduced via means of a plug or other skull portal device 60 such as a burr hole plug 61 which is configured to be placed and secured into a burr hole BH (as shown in FIGS. 2a and 2b). Typically, plug 60 includes a locking device 62 such as a clamp or other fixation mechanisms which locks or fixes introducer 20 to the plug 60 so that introducer 20 does not move after insertion. Introducer 20 can also be stabilized by a flange 64 on plug 60 (or other suitable structure or mechanism). One or more of the plug, introducer or locking device can contain a sensor 63 to detect movement of the introducer or otherwise detect an unlocked state of the introducer or if it has otherwise become loose. Suitable sensors 63 include contact sensors, hall effect switches, accelerometers and like devices. Sensors 63 can be coupled to circuitry in control module 80 discussed herein to alert the patient or medical care giver if introducer 20 is no longer in a fixed state. This circuitry can include various filters (e.g., low pass, high pass, etc.) to filter out movement attributed to normal head and body motion from movement attributed to the loosening of introducer 20 from the locking device 62.

Distal introducer end 22 may be configured with a tapered, or other related shape and can be tissue penetrating to facilitate introduction into brain tissue. The introducer may also be configured to track over a guide wire (not shown) which is advanced through a lumen 25 so as to facilitate placement of the distal end 22 at a selected target tissue site TS in the brain. Placement at the target site TS can also be facilitated by use of one or more radio-opaque or echogenic markers 26 which can be positioned at one or more locations on the introducer including distal end 22. Markers 26 allow the introducer to be advanced under fluoroscopic observation or other imaging modality. All or a portion of introducer 20 can comprise various biocompatible polymers known in the art including without limitation polyethylene, PET, PEBAX, PTFE, silicone, polyurethane and combinations thereof. These materials can also comprise one more radio-opaque materials known in the art including titanium dioxide.

As shown in greater detail by FIG. 3, introducer 20 includes one or more lumens 25, which can be configured for advancement of electrode members 30, guide-wires, viewing scopes, lights sources and like devices. Lumens 25 can also be configured for providing suction as well as infusion of various solutions including one or more medicaments solutions (e.g., a solution containing a loop diuretic such as furosemide) for treatment of epilepsy, migraine and other brain related conditions and diseases. Each lumen 25 can also include a port 27 positioned at distal portion 20*dp* of introducer to allow for the passage of electrode member 30, as well as fluids and medicaments. In many embodiments, the introducer can include separate lumens 25 for each electrode member 30. This allows for independent advancement of electrode members 30. As is discussed herein, in many embodiments, the distal portion of members 30 can include a bend or curve 30*b*. This can be achieved by configuring the distal portion 25*d* of lumens 25 to have an internal bend 25*b* which can correspond to the amount of desired bend in member 30. In various embodiments, the angle 25*ba* of bend 25*b* can be in the range from 20 to 90°, with specific embodiments of 30, 40, 45, 50, 60, 70 and 80°.

Referring now to FIGS. 4A, 4B, 4C and 5, one or more embodiments provide that all or portion of electrode members 30 are advanceable in a single lumen 25. In these and related embodiments, the bend 30*b* in members 30 can be achieved through use of a deflector 50 which deflects the electrode members as they are advanced out of the introducer. Typically, deflector 50 will be positioned in distal portion 25*dp* of lumen 25 but it can also be positioned in other locations as well. Deflector 50 comprises a series of individual channels 51 which direct electrode members 30 at a selected angle to achieve the desired amount of bend. Typically, the deflector will include at least three channels 51 with additional numbers are also contemplated. Desirably channels 51 are radially equally distributed about the longitudinal axis 201 of the introducer (e.g., for three members they may be approximately 120° apart). Also, they may formed in the body 52 of the deflector 50 and run along the length of the deflector from the proximal 53 to distal portions 54 of the deflector. The proximal end 55 of the deflector is desirably shaped to deflect electrode members 30 into the channels 51 as they are advanced through lumen 25. Also channels 51 are desirably sized so that only one electrode member 30 will fit into a channel. In use, these two features confer a self guiding capability to the deflector 50 so that the user can separately or collectively advance the desired number of electrode members 30 into the introducer and have them be guided into separate channels 51. In other embodiments, channels 51 can themselves be deflectable (e.g., through the use of piezo electric or other like materials which can be deflected by electric current) so that user can select and even modify the amount of bend in the deployed members 30. In use, such a feature would allow the user to change the amount of bend in members 30 while observing their position under fluoroscopic or other imaging modality so as to achieve and confirm a desired orientation of the electrode members. Such a feature would also allow the medical care giver to change the direction and orientation of members 30 so as to optimize or tune their detection capabilities to detect a foci F of ANEA in a particular area of the brain.

Figure 7A:
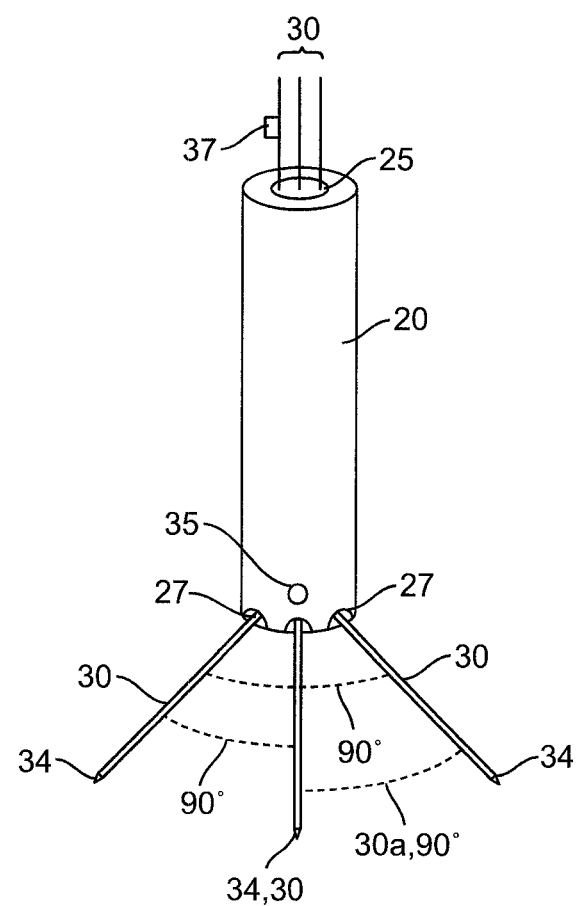
FIG. 7a is a perspective view showing an orthogonal orientation of the electrode members in the deployed state.
Figure 7B:
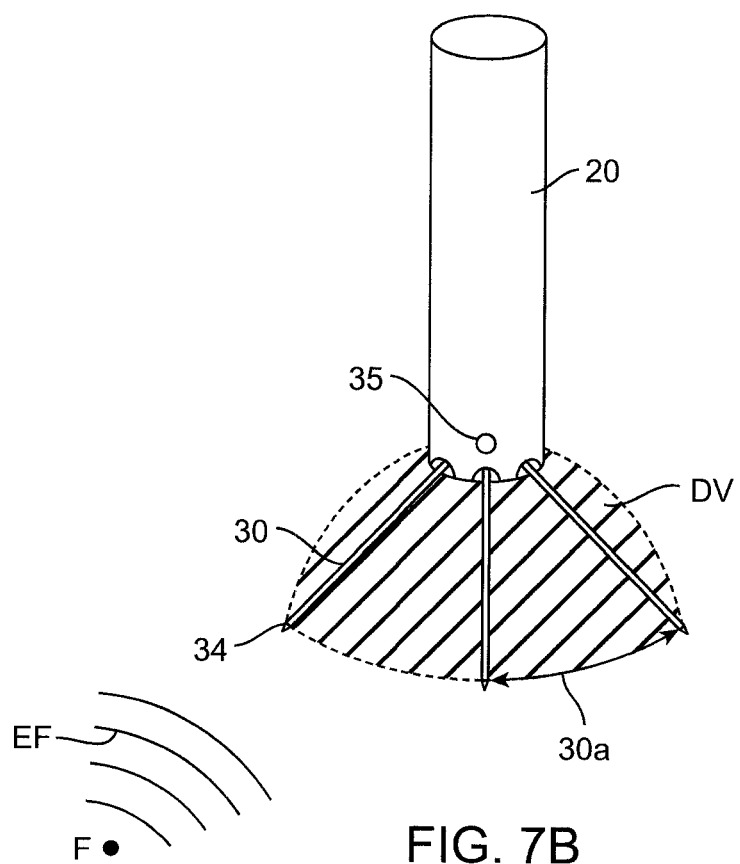
FIG. 7b is a perspective view showing the orientation of the electrode members and the detection volume defined by them in the deployed state.

Referring now to FIGS. 6a, 6b, 7a, 7b, 8a, and 8b, one or more embodiments provide that electrode members 30 have a non-deployed state when positioned in the introducer (as is shown in FIG. 6a) and a deployed state when advanced out of the introducer as shown in FIG. 6b. In the deployed state, the electrode members have an orientation which can detect a foci F of aberrant neural-electric activity. In one embodiment, this is achieved by configuring the electrode members to have a substantially orthogonal orientation with respect to each other. More specifically, with respect to the longitudinal axis 301 of each electrode member, so that the angle 30*a* between electrode members is approximately 90° so as to define a three dimensional Cartesian coordinate axis system which corresponds to a detection volume DV as shown in the embodiments of FIGS. 7a and 7b. As will be discussed herein, this configuration allows the electrode members to measure voltages produced by an electric field EF generated by Foci F so as derive the electric field vector $\vec{E}$ including the direction and magnitude of the vector. For orthogonal orientations, the defined detection volume DV is substantially tetrahedral is shown in the embodiment of FIG. 7b. Other orientations defining other detection volumes DV are also contemplated such as various polyhedral shapes. For example, four electrode members can be configured to define a substantially pyramidal detection volume. Still additional numbers of electrode members such as six or more can be configured to define a detection volume which approaches a substantially conical shape.

Figure 8A:
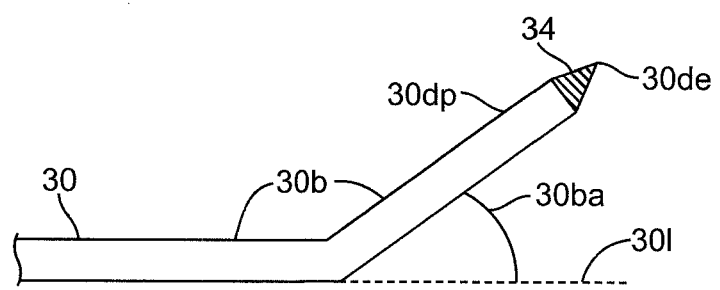
FIGS. 8a and 8b are side views illustrating embodiments of a bent electrode.
Figure 8B:
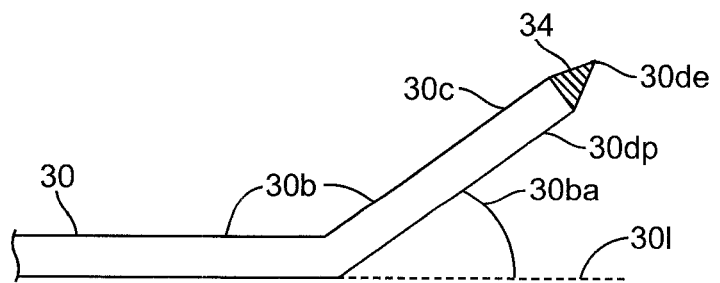

In the non-deployed state within the introducer, electrode members 30 are in a compacted state and substantially straight. As electrode members 30 are advanced out of distal end 22 they become distended so as to define a volume DV for detection of Foci F. The electrode members may include a bent shape 30b when advanced out of introducer 20. This can be accomplished by fabricating the electrode members to have spring memory to assume the bent shape 30b when advanced out of introducer 20. The bent shape 30b can also be accomplished by advancing the electrode members through bent lumens 25 or a deflector 50 as is described herein. The angle 30ba of the bend 30b can be in the range from 20 to 90°, with specific embodiments of 30, 40, 45, 50, 60, 70 and 80°. Bend 30b can be substantially abrupt as is shown in the embodiment of FIG. 8a or can have a selected amount of curvature to confer a curved shape 30c to the deployed portion 30dp of the electrode member as is shown in the embodiment of FIG. 8b.

Figure 9:
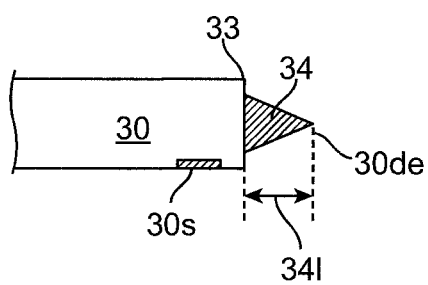
FIG. 9 is a side view illustrating an embodiment of the electrode member including an insulating sleeve and a conductive core.
Figures 10A, 10B:
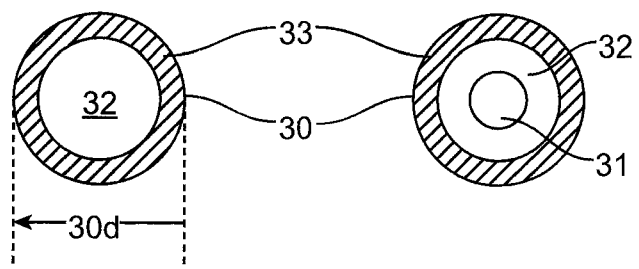
FIGS. 10a-10b are cross sectional views of embodiments of the electrode member.

Referring now to FIGS. 9, 10a, and 10b, typically, the electrode members 30 will comprise a conductive core 32 and an outer insulating sleeve or jacket 33 extending along most of the length of the electrode member so that the only tissue contacting conductive portion 34 of the electrode member is the distal end 30de. The length 341 of the conductive portion 34 will be 1 mm or less, though longer portions are also contemplated. In one or more embodiments, the length is in the range from about 0.75 to about 0.25 mm. The insulating sleeve 34 can comprise various insulating biocompatible polymers known in the art such as silicone and polyurethane. Sleeve 34 can also have lubricous properties to facilitate advancement of the electrode members into tissue. Also, sleeve 34 can contain various drug eluting compounds known in the art to reduce bio-adhesion to the sleeve (both cells and molecules). The conductive core 32 of the members 30 can be fabricated from various biocompatible conductive materials known in the art including metals and conductive polymers and like materials. An example of a suitable metal includes 304V steel. In preferred embodiments, members 30 comprise a shape memory material such as NITINOL. For particular shape memory embodiments, the advanced electrode members 30 can assume their deployed state as they are warmed by the brain tissue above the transition temperature of the selected shape memory material.

In many embodiments, the distal ends 30de of the electrode members have a pointed or other tissue penetrating shape to facilitate advancement into tissue. Also, desirably, electrode members 30 have sufficient stiffness to be advanced into tissue, but are sufficiently flexible to assume a curved shape when advanced out of the introducer. The stiffness and flexibility can be achieved by selection of the member diameter, material and material treatment (e.g., annealing) as is known in the medical guide-wire arts. In various embodiments, the diameter 30d of the electrode members can be in the range of 0.0005 to 0.018" with specific embodiments of 0.001, 0.005, 0.010 and 0.015". Typically, the electrode member 30 will be solid as is shown in the embodiment of FIG. 10a; however, in various embodiments, members 30 may have a lumen 31 as is shown in the embodiment of FIG. 10b. Lumen 31 can be used for intracranial delivery of one or more medications including both solid and liquid form medications. In such embodiments, members 30 can be fabricated from various hypotubes known in the art. Also in various embodiments members 30 may also include one or more sensors 30s for measuring various tissue properties which may be predictive of seizure or pre-seizure events. Accordingly, such sensors can include without limitation, pH, temperature, $pO_2$, $pCO_2$, glucose, and other biochemical related sensors. Measurements from such sensors can be combined with voltage/electric field vector measurements as means for determining pre-seizure and seizure events.

Figure 11:
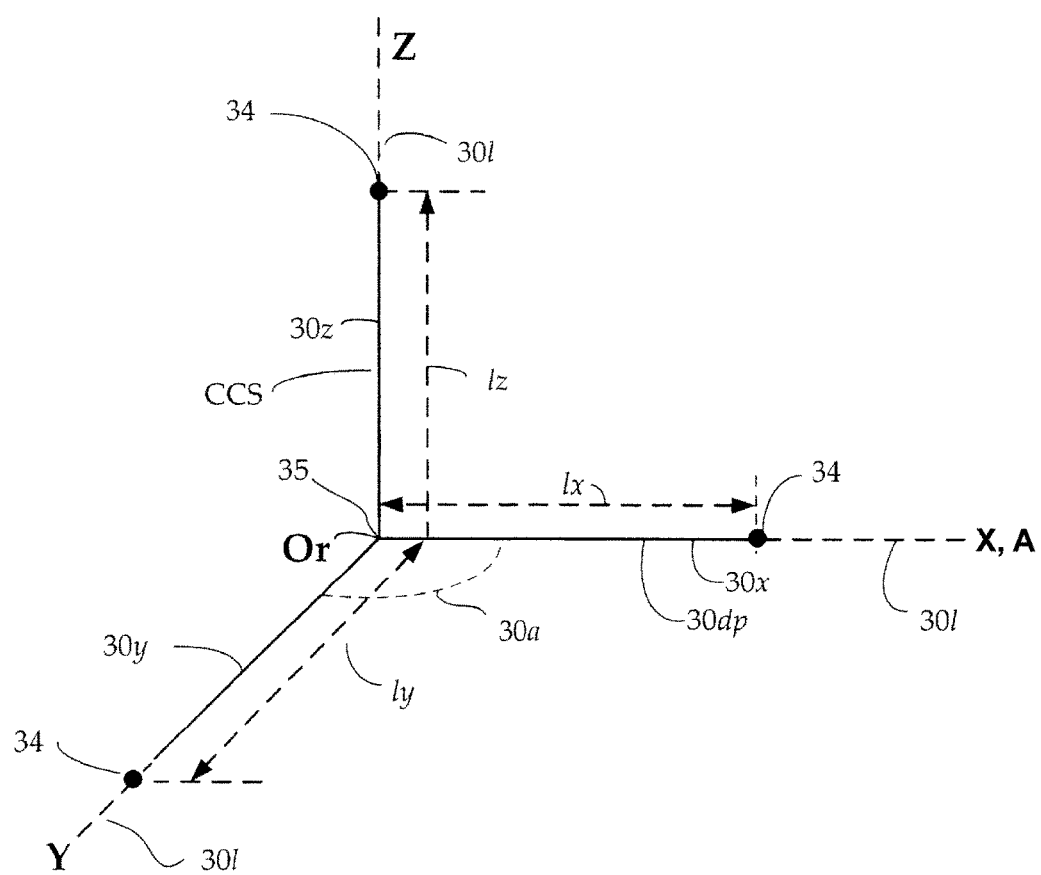
FIG. 11 is a graphical view illustrating alignment of the electrode members with a Cartesian coordinate system.
Figure 12:
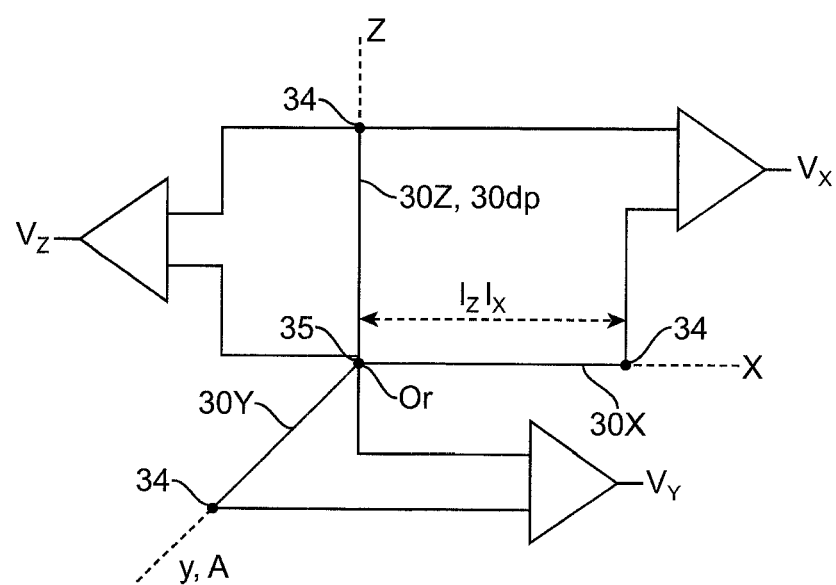
FIG. 12 is a combination graphical and schematic view illustrating alignment of the electrode members with a Cartesian coordinate system and generation of voltages the electrode members as a result of abnormal neural-electric activity.

Referring now to FIGS. 11-12, in many embodiments, the deployed portions 30dp of the electrode members 30 (i.e., that projecting out of the introducer 20) can have a substantially orthogonal orientation such that each electrode member 30 is oriented with an axis A of a Cartesian coordinate system CCS. The origin Or of the axes corresponds to the position of reference electrode 35 which typically will be at the distal end 22 (FIG. 6a) of introducer 20. This results in an x, y and z electrode member 30x, 30y and 30z. Each of these oriented electrode members project a selected distance l past reference electrode 35 resulting in distances $l_x$, $l_y$ and $l_z$ which in preferred embodiments are substantially the same. The electric field EF (FIG. 7b) generated by Foci F results in voltages $V_x$, $V_y$ and $V_z$ at respective electrode members 30x, 30y and 30z. The actual voltage being due to the potential difference between tissue contacting conductive portion 34 and reference electrode 35 which is typically positioned near introducer distal end 22). In many embodiments, electrode members 30x, 30y and 30z can share a common reference electrode 35 or each may have its own.

Figure 13:
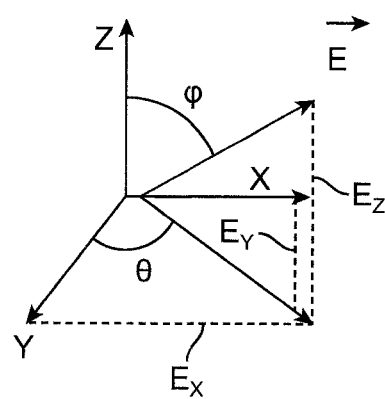
FIG. 13 is graphical view illustrating an electric field vector produced by aberrant neural-electric activity and its polar components.

A discussion will now be presented of the mathematical methods used to calculate the components of the electric field vector $\overline{E}$ generated by a foci F of abnormal neural-electric activity and the subsequent direction D of foci F relative to the distal end the introducer. These and other related methods along with equations 1-6 can be incorporated into algorithms 83 described herein. Referring now to FIGS. 11-13 and equations 1-6 below, electric field vector $\overline{E}$ has a magnitude E having scalar components $E_x$, $E_y$ and $E_z$ and angular directions θ and φ. Measurement of voltages $V_x$, $V_y$ and $V_z$ by electrode members 30x, 30y and 30z allows calculation of $E_x$, $E_y$ and $E_z$ using equation (1), the magnitude of the vector $\overline{E}$ can be calculated by equation (2). Equations 4-6 allow determination of the direction of vector $\overline{E}$ relative to origin Or (and hence the direction relative to introducer distal end 22) by virtue of determination of angles φ, and θ. Determination of this direction, then allows determination of the direction D of Foci F (relative to introducer distal end 22) from which vector $\overline{E}$ emanates.

$$E_x = V_x/l_x, \; E_y = V_y/l_y, \text{ and } E_z = V_z/l_z \tag{1}$$

$$|\overline{E}| = (E_x^2 + E_y^2 + E_z^2)^{1/2} \tag{2}$$

$$\cos \varphi = (E_z/|\overline{E}|) \tag{3}$$

$$\varphi = \cos^{-1}(E_z/|\overline{E}|) \tag{4}$$

$$|\overline{E}|*\sin \varphi * \cos \theta \tag{5}$$

$$\theta = \cos^{-1}(|\overline{E}|*\sin \varphi)/E_y \tag{6}$$

Figure 14:
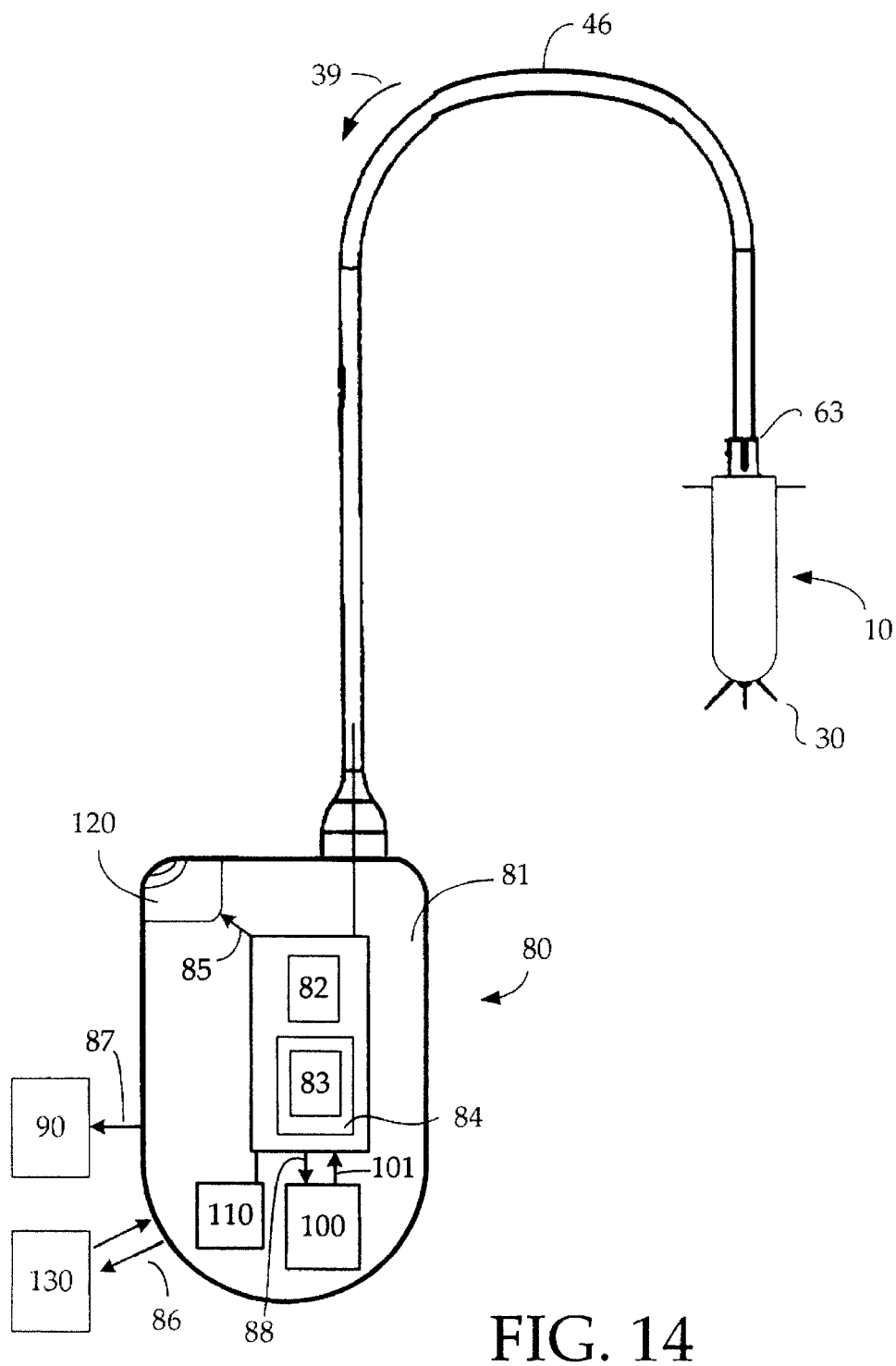
FIG. 14 is a block diagram showing an embodiment of a control module for use with various embodiments of the ANEA detection apparatus.
Figure 15:
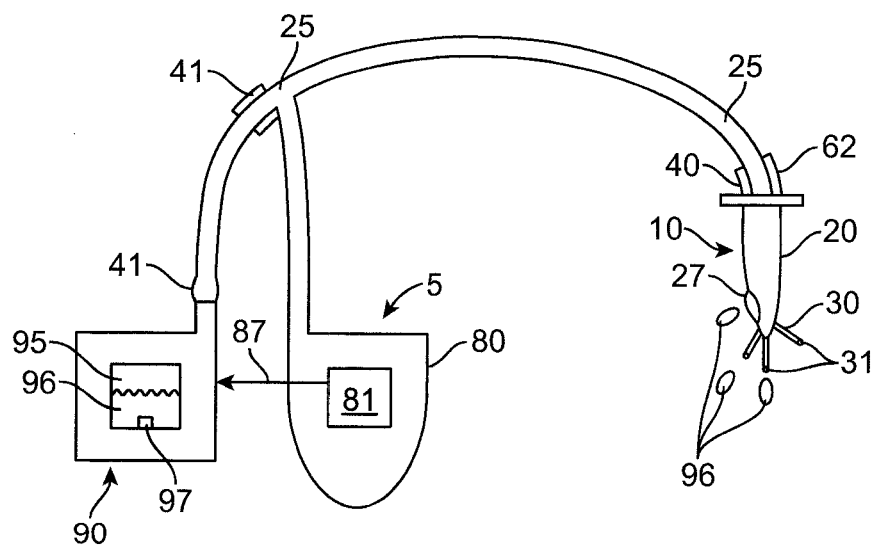
FIG. 15 is a block diagram/side view of an embodiment of the drug delivery device.
Figure 16A:
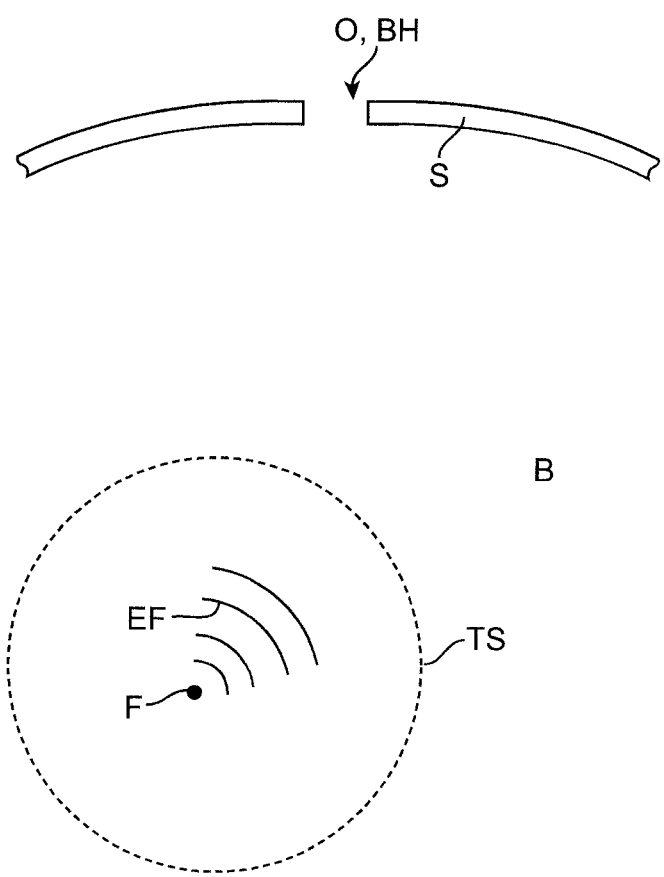
FIGS. 16a-16e are side views illustrating a method for introduction of the introducer and deployment of the electrode members to detect a Foci of aberrant neural electric activity in a target tissue site in the brain.
Figure 16B:
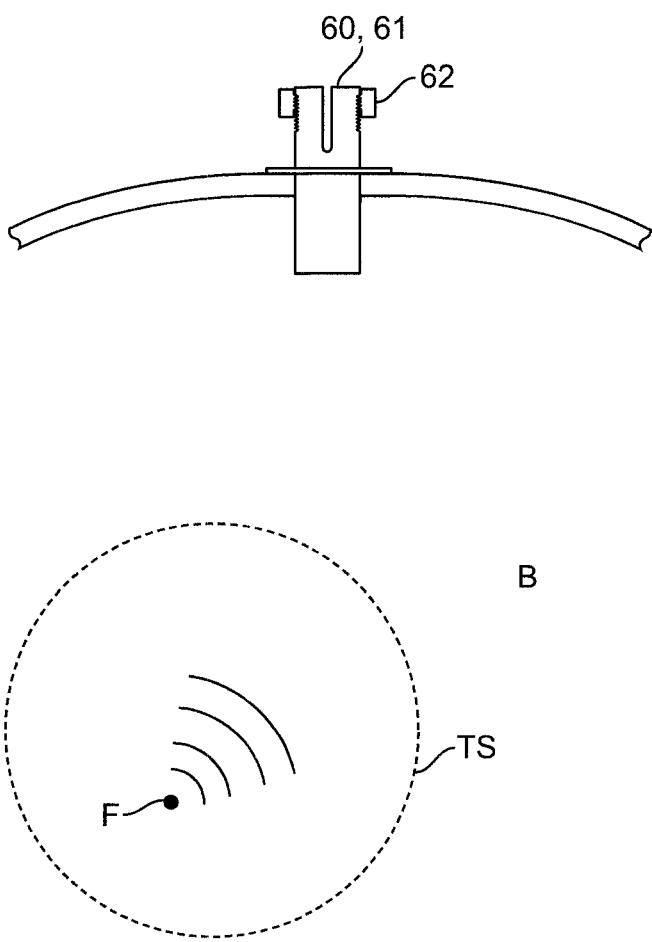
Figure 16C:
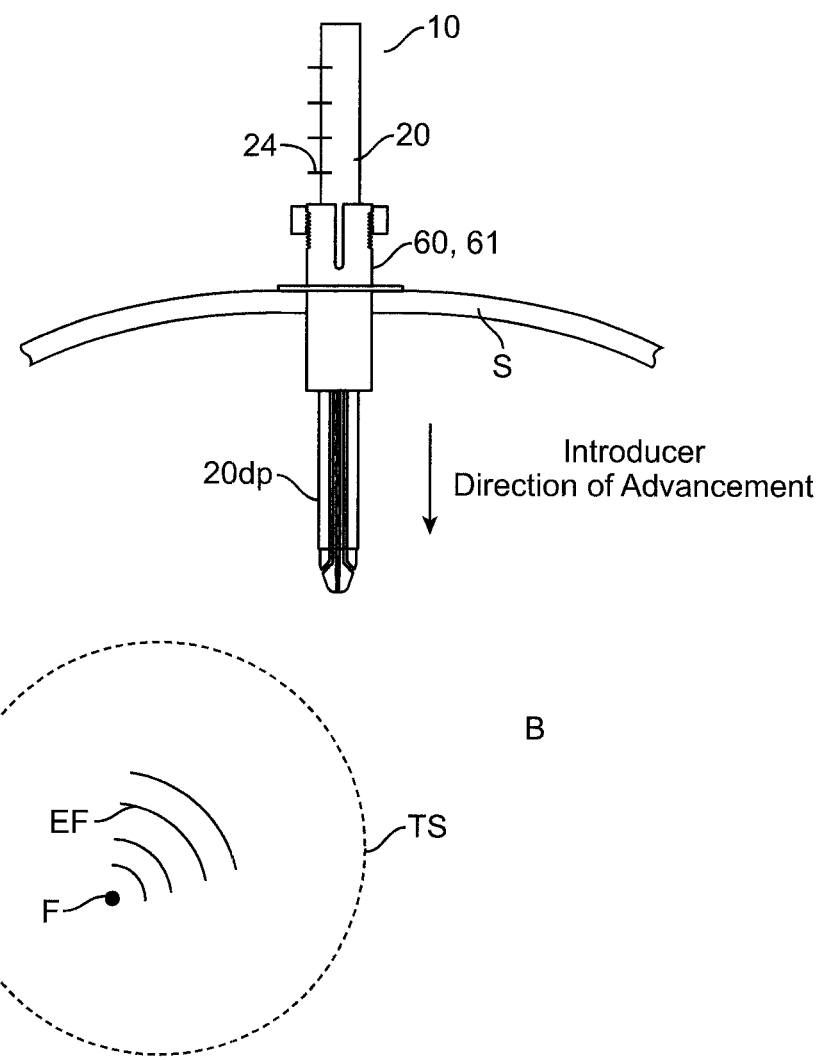
Figure 16D:
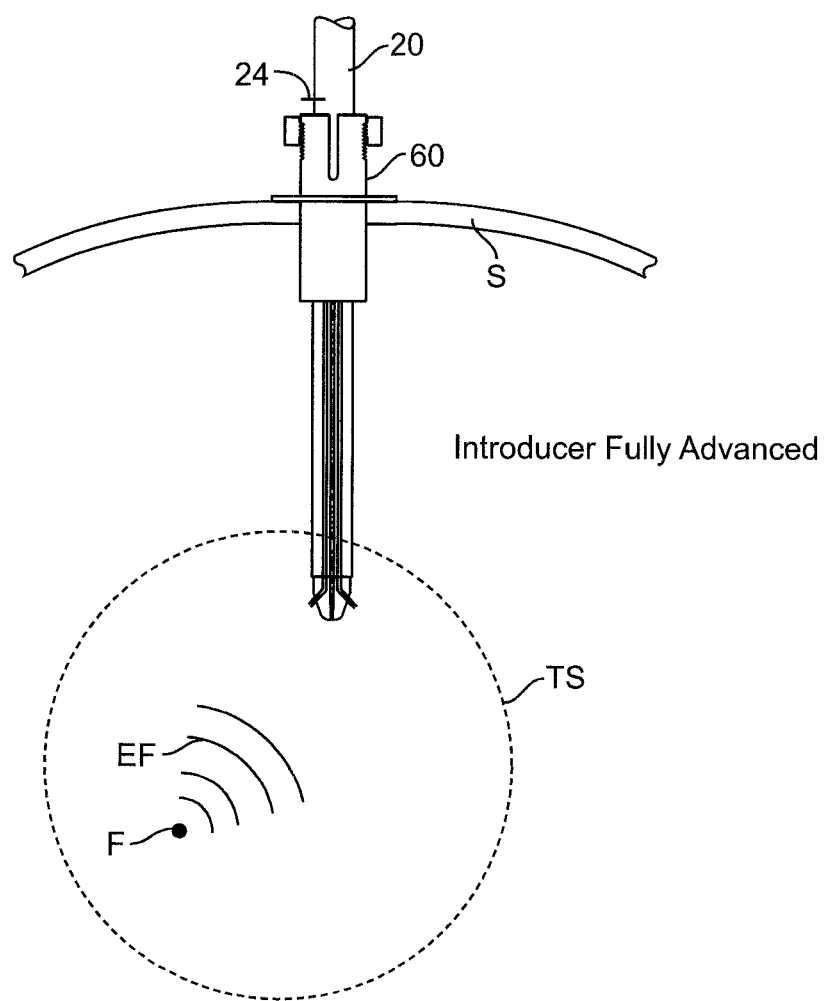
Figure 16E:
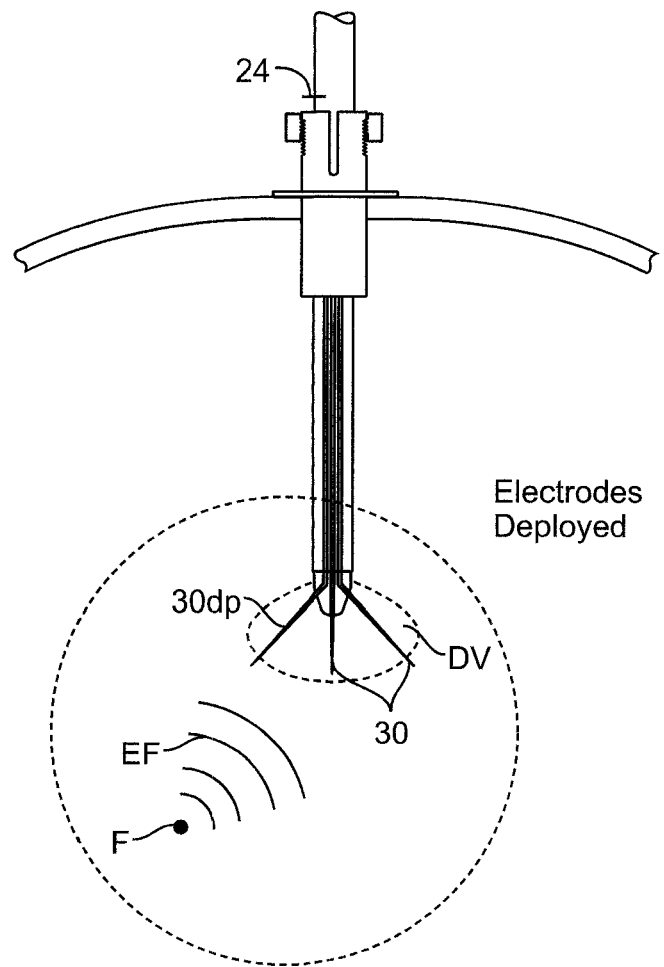

Referring now to FIG. 14-15, in many embodiments, apparatus 10 can be coupled to a control module 80 (see FIG. 1) (hereinafter module 80) that is configured to perform one or more functions. These can include storage and analysis of signals received from electrode members 30, sensors 63, detection of a pre-seizure or seizure event, alerting the patient and medical care provider of an impending seizure and control of various interventional actions to prevent a seizure including drug delivery and electrical stimulation of brain tissue. Module 80 can include one or more processors, state devices, circuits (e.g., power control, filters, etc.) alarms, batteries and other power storage devices. It can also include one or more communication resources 110 such as an RF communication chip for wirelessly communicating with external medical monitoring instrumentation using MICS or other medical wireless communication protocol. Module 80 may also be coupled to or include an integral drug delivery device 90 as well as brain stimulator 100 described herein. Control module 80 can be worn by the patient or may be configured to be implanted subcutaneously in the head and neck area (as shown in FIGS. 2a) or other area in the body.

Module 80 will typically include at least one controller 81 which can comprise various logic resources 82 such as a processor, state device or a combination of both. Processor 82 can be off-the-shelf (e.g., such as those manufactured by Intel® or Texas Instruments®) or can comprise a custom chip such as an ASIC. Controller 81 may include one or more algorithms 83 which can be implemented through software, hardware or a combination of both. For software implementation, algorithms 83 can be stored in memory resources 84 (e.g., ROM, RAM, DRAM, etc) integral or coupled to logic resources 82. Algorithms 83 can be configured to perform a number of functions including without limitation: processing and storage of signals 39 received from electrode members 30; sensors 30s or 63, calculation of the components of an Electric Field vector $\vec{E}$ including the magnitude and direction D of the vector, detection of one or more of ANEA, a pre-seizure or seizure event; alerting the patient and medical care provider of an impending seizure and communicating with external medical monitoring instrumentation; and control of various interventional devices and actions to prevent a seizure such as drug delivery and electrical stimulation of brain tissue. As is described herein, various detection algorithms 83 can be configured to generate a detection score indicative of whether a pre-seizure or seizure event is occurring. Algorithms 83 can be configured to include one or more signal processing algorithms known in the art such as Fast Fourier Transforms, wavelet, fuzzy logic and like algorithms.

In many embodiments, module 80 includes a stimulator device or stimulator 100 configured to send an inhibitor signal 101 via electrode members 30 (or other implanted electrode) to prevent the onset of a seizure or stop an occurring seizure or otherwise reduce its duration. Stimulator 100 will typically comprise power control and charging circuitry and a discharging capacitor or other dischargeable power voltage source. It can also include various pacing and/or signal processing circuits to as to provide a duty cycle of inhibitory signals over an extended period of time.

Drug delivery device 90 can comprise one or more drug pumps known in the art including for example, displacement pumps (e.g., a piston pump), peristaltic pumps, screw pumps and like devices. It can be miniaturized for implantation in the head or neck area of the patient (e.g., at the base of the skull as shown in FIGS. 2a and 2c) or other portion of the body. Miniaturized pumps can comprise MEMs and/or bubble jet based miniature pumps. Also device 90 can be configured for one or both of intracranial or IV delivery. For intracranial delivery device 90, can be fluidically coupled to one or more lumens 25 of introducer 20 via connectors 40 and 41 so as to deliver the drug (either in liquid or solid form0 through lumen 25 and/or through lumens 31 of hollow embodiments of electrode members 30. Connectors 40, 41 can include luer-lock, connectors, Touhy Borst adapters and other like devices. Delivery device 90 can also be configured for the delivery of liquids, solids or both. For liquid delivery, the device 90 can use one or more of displacement, rotary or peristaltic pumping devices. For solid delivery, a miniature screw pump can be used with other solid form delivery mechanisms contemplated. Typically, the device 90 will also include a reservoir 95 containing of one or more medicaments 96 (also referred to herein as medication 96) which may comprise solid, liquids, or both. Whatever the form, reservoir 95 desirably contains a plurality of doses of medication 96 sufficient for a prolonged time period. For embodiments where medicament 96 is in solid form, reservoir 95 may contain up to 500 or more doses of medication 96. In other embodiments, reservoir 95 can also be separate from delivery device 90 though still coupled to it (e.g., fluidically or otherwise) via a catheter or like connecting member. In the later case, the reservoir 95 can be implanted subcutaneously or can even be positioned external to the body to allow for easier replenishment of drug (e.g., via injection through the skin) Delivery device 90 is also desirably configured to be controlled by signals 87 from module 80 and controller 81. Reservoir 95 can also include one more sensors 97 configured to sense the amount of drug (liquid or solid) remaining in the reservoir as to alert the patient or doctor when the reservoir needs to be replenished.

In one or more embodiments, the invention may provide a drug delivery system 105 shown in the embodiment of FIG. 2c for the intracranial delivery of one or more drugs to various regions within the brain such one or more ventricles within the brain (various components of system 105 which may correspond in or more aspects to system 5). Such drugs may include those for the treatment of one or more neurological conditions such as epilepsy, migraine headaches and depression. According to one or more embodiments, system 105 comprises a drug storage and delivery device 130 coupled to a drug delivery member 120 as is shown in the embodiments of FIGS. 2c and 2d. Delivery member 120 has a proximal end 121 coupled to device 130 and a distal end 122 positioned at or near a delivery site DS in the brain B, such as the ventricle V or other location. In various embodiments delivery member 120 may correspond to connector 45 and drug storage and delivery device 130 to device 90 and/or 80. As discussed further herein, storage and delivery device 130 is configured to be implanted subcutaneously, typically in the back or side of the patient's head or other location in or one the patient's body. Delivery member 120 desirably has sufficient length to extend from the back of the patient's head/skull or other implant location into the patient's brain to reach a delivery site DS including a site within a deep brain region of the brain. Further description of various drug delivery apparatus, systems and methods which may be used in one more embodiments of the invention may be found in U.S. patent application Ser. Nos. 13/645,344 and 13/681, 825, the disclosures of which are incorporated by reference herein in their entirety for all purposes.

The drug delivery member 120 will typically comprise a catheter 120 or other like flexible member having one or more lumens 123 which have an internal diameter sized for delivery of solid form drug 200 such as drug pellet 200 to a delivery site DS in the brain such as a ventricles in the brain. All or a portion of catheter 120 can be configured to be subcutaneously implanted under the patient's scalp so that it can extend from device 130 to delivery site DS in the patient's brain. Accordingly, catheter 120 may comprise any number of biocompatible resilient polymers known in the art (e.g., silicone, PeBax, polyurethane, polyethylene (e.g., HDPE, LDPE), etc.) and may be formed using various extrusion methods also known in the art. Further, the catheter may be sized (e.g., diameter) and otherwise configured (e.g., from resilient biocompatible materials) so that when implanted underneath the patient's scalp, it is minimally visible and/or does not impact hair growth or condition of the scalp. Further, the portions of catheter 120 which are implanted within the brain, including distal tip 120d are configured and otherwise structured to be atraumatic and unreactive with brain tissue. Such materials for the brain implanted portions of catheter 120 can include various silicones and polyurethane polymers. In one more embodiments, all or a portion of catheter 120 may be constructed from similar materials as those used in cerebral-spinal shunts.

In many embodiments, the drug delivery system 105 further comprises a diffusion chamber 300 coupled to the distal end 122 of the drug delivery member or catheter 120 as shown in FIGS. 2e1-2e4. The drug delivery member 120 can be delivered into the brain such that the diffusion chamber 300 is positioned in a selected ventricle(s) of the brain. As described herein, the diffusion chamber 300 may facilitate the controlled release of drug into the CSF present in the ventricles of the brain. Furthermore, the diffusion chamber 300 and the drug delivery member 120 may have sufficient flexibility such that during advancement into the brain, the diffusion chamber 300 and at least the distal portions of the drug delivery member 120 can conform to the shape of the ventricle to which they are delivered. By conforming in such a manner, the delivered diffusion chamber 300 and drug delivery member 120 do not deform the ventricular walls of the brain sufficiently to cause any significant physiological effects. The flexibility of the diffusion chamber 300 or the drug delivery member 120 or both can allow the diffusion chamber 300 to deform up to 30 degrees or more when advanced against a ventricular surface. Typically, the delivered diffusion chamber 300 and drug delivery member 120 do not deform the ventricular walls of the brain by more than 3 mm and applies no more than about 20 mmHG of pressure to the ventricular wall.

The diffusion chamber 300 and the drug delivery member 120 can be configured such that they may deform sufficiently to be advanced through the ventricular anatomy of the brain to reach a selected ventricle. For clarity, the ventricular anatomy of the brain is described in a section below with reference to FIG. 19. The selected ventricle can include any of the major ventricles of the brain, including for example, the left ventricle LV and the right ventricle RV (including their inferior and posterior horns), the third ventricle TV, and the fourth ventricle FV. Also, during such advancement and positioning, the flexibility of the catheter 120 and the diffusion chamber 300 can be desirably configured such that they do not deform a ventricular wall of the brain sufficiently to cause any significant physiological effects. These physiological effects may include a decrease in the production of CSF (e.g., below 21 ml/hr, preferably below 20 ml/hr) or a neurological effect such as a loss of consciousness, pain or numbness, vomiting, change in heart or respiration rate, etc.) CSF production can be measured using spinal tap procedures and/or various imaging modalities.

Referring back to FIG. 2e1, the diffusion chamber 300 may comprise a flexible tube having one end attached to the open distal end of the catheter and its distal end 310 closed. The diffusion chamber 300 defines an inner volume or lumen 315 into which medication, for example in the form of a medication or drug pellet 200, may be placed and retained. When placed in the ventricles of the brains, CSF can diffuse into the inner volume 310 through holes or other openings 305. The CSF can dissolve the medication. The CSF with medication dissolved therein can then diffuse out through the same holes 305. In some embodiments, the interior wall of the inner volume 315, including the openings into the holes 305, is lined with a membrane that would regulate the diffusion rate of the drug.

When advanced through the brain, the diffusion chamber 300 and the catheter 120 may become bent or curved. Therefore, in some embodiments, the catheter 120 may further comprise an inner lining of coiled wire 120s to help maintain the patency of the catheter 120 (FIGS. 2e2, 2e3), particularly when the catheter 120 is put into a bent or deformed position, such as when it conforms to the shape of a ventricle. The wire lining 120s can allow a medication or drug pellet 200 to be delivered to the diffusion chamber 300 even when the catheter 120 is deformed or bent. The diffusion chamber 300 may be made of any number of flexible materials, including PEBAC and various elastomers such as silicones and polyurethanes and co-polymers thereof. Other embodiments may employ various superelastic metals known in the art, such as Nitinol.

As shown in FIGS. 2e1 and 2e4, there can be four rows of eight holes 305 each for a total of thirty-two (32) holes 305. Each row is offset 90 degrees away from the adjacent rows. More or less holes 305 may be provided depending on the length and width of the diffusion chamber or to achieve a desired CSF diffusion rate, drug diffusion rate, or drug disintegration rate. For example, there may instead be two rows of sixteen holes or slits each, with each row being offset 180 degrees away from each other. The size of the holes 305 may vary from 0.004 inch (0.1 mm) diameter to 0.02 inch (0.5 mm) diameter. The diffusion chamber 300 may have an internal diameter of 0.04 to 0.10 inches (1 to 2.5 mm), and outer diameter of 1.5 to 4.5 mm, and be 2 to 20 mm in length.

Instead of holes 305, slits 306 may be provided on the diffusion chamber 300 instead (FIG. 2f1, 2f2). Like the holes 305, the slits 306 may be distributed in multiple rows, with more or less slits 306 per row depending on the length of the diffusion chamber 300. The slits may have a width in a range of about 0.1 to 0.5 mm and a length in the range of about 0.25 to 5 mm.

In some embodiments, the diffuser or diffusion chamber may be a wire basket or cage 301 coupled to the distal end 122 of the catheter 120 (FIG. 2g1). This wire basket or cage 301 would hold a medication pellet and allow CSF to rapidly flush the medication into the CSF in the ventricles of the brain. The winding of the wire basket or cage 301 may be configured to allow sufficient space for the CSF to weep in and the drug solution to weep out. The wire basket or cage 301 may be constructed from titanium, MP35N®, 35NLT®, or 316L stainless steel. The wire size could range from 0.002 to 0.006 inches (0.05 to 0.15 mm) in diameter. The inside diameter of the wire basket 300 could be from 0.04 to 0.10 inch (1 to 2.5 mm) and the wire basket 30 could be from 0.08 to 0.8 inch (2 to 20 mm) in length.

In some embodiments, the diffuser, diffusion chamber, or diffusion section may also comprise various porous materials. For example, the diffuser may comprise a closed-ended tube 302 coupled to the distal end 122 of the catheter 120 as shown in FIG. 2g2. The diffuser 302 may have a flexibility such that it can conform to the ventricles of the brain (e.g., the shape or contour of the ventricular wall) without causing any significant physiological effects much like the other diffusion chambers described herein. The diffuser 302 may in some embodiments comprise a number of holes or slits or may in other embodiments simply be uniform throughout its exterior. The various porous materials which may comprise the diffuser 302 can comprise any number of porous biomaterials such as various polymeric fiber materials such as polyethylene teraphalate (PET) or Nylon. In preferred embodiments of a porous diffuser 302, the diffuser may be fabricated from Dacron, such as a Dacron mesh, which can be either woven or knitted. The size and porosity of the porous material can be selected to allow CSF to seep or diffuse in or out of the diffuser at a selected rate to in turn achieve a selected rate of disintegration of the drug pellet and/or rate of diffusion of drug from the diffuser 302. The size and porosity for achieving this can be determined using various porosity measurement techniques known in the art. According to one or more embodiments, the porous section can have a uniform porosity so as to wick in CSF and diffuse out drug solution uniformly from substantially the entire area of the diffuser 302. According to other embodiments, the diffuser 302 can be fabricated from porous materials having varying porosity so as to preferentially wick in CSF and weep out drug solution from specific portions of the diffuser.

FIGS. 2h1, 2h2 show side views of another embodiment of a diffusion chamber 300a. The diffusion chamber 300a may be similar in many respects to the diffusion chamber 300 described above, including being made of similar materials and having similar dimensions, components, conformability, and other properties. In these and related embodiments, the diffusion chamber 300a further comprises an elongated proximal portion 320 which is mounted onto the distal end 122 of the drug delivery member or catheter 120 as shown in FIGS. 2h3, 2h4.

FIGS. 2i1, 2i2 show side views of another embodiment of a diffusion chamber 300b. The diffusion chamber 300b may be similar in many respects to the diffusion chamber 300a described above, including being made of similar materials and having similar dimensions, components, conformability, and other properties. The diffusion chamber 300b, however, has a shorter distal drug diffusion portion as certain ventricles may not be enlarged enough to require a longer distal drug diffusion portion. The diffusion chamber 300b comprises three rows of three holes 305 each. The inner volume 315 of the diffusion chamber 300b may allow for approximately three medication pellets of 1.5 mm in length. The size of the hole may be 0.010 inches, which is approximately a quarter of the diameter of the intended pellet, so that the pellet will not prematurely exit the diffusion chamber 300b.

FIGS. 2j1, 2j2 show side views of another embodiment of a diffusion chamber 300c. The diffusion chamber 300c may be similar in many respects to the diffusion chamber 300b described above, including being made of similar materials and having similar dimensions, components, conformability, and other properties. The diffusion chamber 300c further comprises a lower-profile, necked portion 321 on the proximal portion of the distal drug diffusion portion, adjacent to where the diffusion chamber 300c joints the catheter 120. The necked portion 321 may allow the diffusion chamber 300c to bend and flex or otherwise deform to the shape of the ventricles or other structure within the brain as well as provide for other flexible properties described herein. For example, the necked portion 321 may allow the distal tip to bend at an angle of up to 30 degrees as shown in FIG. 2j3. In another example, FIGS. 2j4 to 2j6 also show the diffusion chamber 300c bending as it is inserted into the lateral ventricle LV of a patient. The neck portion 321 facilitates the diffusion chamber 300c conforming to the shape of the lateral ventricle LV, whether the diffusion chamber 300c remains straight (FIG. 2j4), is bent one way (FIG. 2j5), or is bent the other way (FIG. 2j6).

FIGS. 2k1, 2k2, 2k3, and 2k4 show another embodiment of a diffusion chamber 300d. The diffusion chamber 300d may be similar in many respects to the diffusion chamber 300c described above, including being made of similar materials and having similar dimensions, components, conformability, and other properties. The elongated proximal portion 320g of the diffusion chamber 300d is grooved as best shown in FIG. 2k1 (side-view of the diffusion chamber 300d), FIG. 2k3 (front view of the diffusion chamber 300d), and FIG. 2k4 (cross-sectional view of diffusion chamber 300d taken across lines 2k4). As shown in those figures, the diffusion chamber 300d comprises six grooves or channels 323 distributed evenly about the circumference of the diffusion chamber 300d, although other numbers of grooves are contemplated as well. The grooves or channels 323 facilitate the flow of CSF into and out of the diffusion chamber 300d, allowing more dissolved drug to migrate into the cerebral cortex. The grooves or channels 323 on the elongated proximal portion 320g may also extend back to the catheter 120 to facilitate transport of drug proximally through the channels 323 to reach more superficial areas of the brain including surface areas of the brain such as the motor cortex. Transport may occur by diffusion of the drug through channels, and/or by flow of the drug solution through the channels (e.g., by capillary action or other flow phenomena.) The grooves or channels 323 may be treated with various coatings to promote or enhance capillary flow through the channels 323 in a proximal direction along the catheter 120. In use, such channels 323 provide a means for delivering drug to not only the CSF in the ventricles of the brain, but also to other selected areas of brain tissue. This dual site delivery can provide the benefit of producing a centralized (e.g., to CSF in the ventricle) and more localized delivery of drug to treat one or more neurological conditions such as epilepsy where it may be desirable to deliver to two or more sites in the brain.

Figure 5:
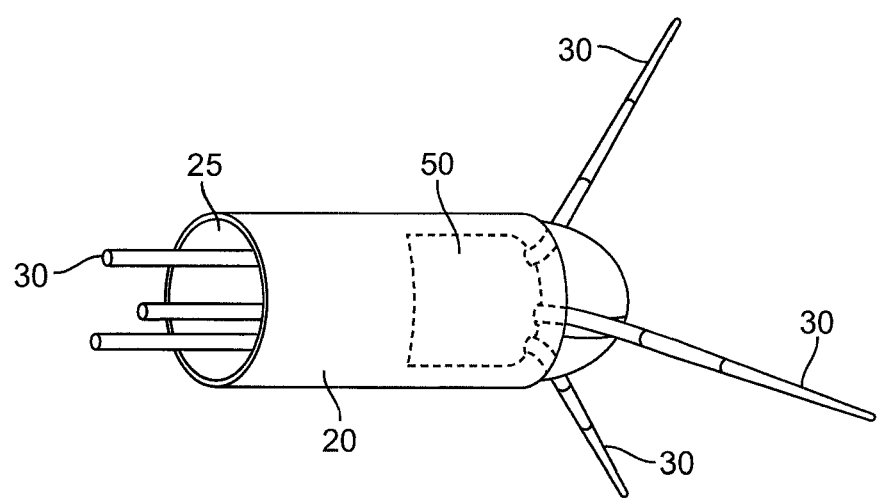

In some embodiments, the grooves or channels 323 may also be disposed adjacent to the holes 315 of the diffusion chamber, for example as shown in diffusion chamber 300d1 in FIGS. 2k5, 2k6. The diffusion chamber 300d1 may be similar in many respects to the diffusion chambers described above, including being made of similar materials and having similar dimensions, components, conformability, and other properties. The grooves or channels 323 in diffusion chamber 300d1 can help maintain the diffusion of the drug or drug solution from the diffusion chamber 300d1 when the diffusion chamber is otherwise in close proximity to the ventricle wall, which may otherwise block diffusion out of the diffusion chamber 300d1. The grooves or channels 323 may be slots, curved channels, or square-shaped channels. In some embodiments, the grooves or channels may be oriented with respect to a longitudinal axis of the diffusion chamber as in FIGS. 2k5, 2k6, but may also have a radial (FIG. 2k7) or other orientation or combination of orientations. In a particular embodiment, the grooves or channels 323 may correspond to convolutions in the walls of the diffusion chamber 300d1, preferably having longitudinal orientation. The convolution may have a sine wave or similar shape with troughs in the sine wave corresponding to the channels 323.

FIG. 2L shows another embodiment of a diffusion chamber 300e. The diffusion chamber 300e is similar in many respects to the diffusion chamber 300 described above, including being made of similar materials and having similar dimensions, components, conformability, and other properties. The diffusion chamber 300e may also have further components, one or more of which may be included in any one of the embodiments of diffusion chambers described herein. The diffusion chamber 300e may further comprise a tubular membrane 325 separating a medication or drug pellet 200d in the internal volume 315 from the openings to the holes 305. This tubular membrane 325 may limit and control the rate of diffusion of the medication from the medication or drug pellet 200d into the CSF. The tubular membrane 325 may be made of polyimide. The diffusion chamber 300e may further comprise one or more release or burp valves 330. The release or burp valves 330 may comprise slits cut into the body of the diffusion chamber 300e. The release or burp valves 330 open when the pressure differential between the internal volume 315 of the diffusion chamber 300e and the exterior of the diffusion chamber 300e rises above a threshold value. Accordingly, the release or burp valves 330 can prevent pressure within the internal volume 315 from building up to a level where diffusion is impeded. The diffusion chamber 300e may further comprise a septum valve 340. The septum valve 340 is disposed on the proximal portion of the diffusion chamber 300e. The septum valve 340 will typically be elastic and self-closing. The septum valve 340 comprises a slit which can allow a medication or drug pellet 200d to be introduced into the internal volume 315 while preventing fluid, such as CSF and CSF mixed with the medication, from exiting proximally into the catheter 120.

Device 130 includes a housing 131 having exterior surface 132 and interior space 133 (also referred to as interior 133). The housing also includes a port 135 for coupling to catheter 120. The housing may be fabricated from one or more biocompatible materials including one or more biocompatible polymers such as ABS, PE, PET; and metals such as titanium. Surface 132 may also be coated with or otherwise comprise one or more compatible materials including for example, silicone, polyurethane or PTFE. Housing 131 may be sized and shaped to be positioned in any number of locations in the head, neck or other area in or one the patient's body. In preferred embodiments, the housing is sized, shaped and otherwise configured to be implanted at the base of the patient's skull or nearby area.

Device 130 contains a drug store 140 having a plurality of doses 200d of medication 200 which are typically positioned within housing 131. Medication 200 comprises a drug other therapeutic agent 210 for treatment of a neurological condition and one or more excipients 220 as is described in further detail herein. Doses 200d may comprise solid and/or liquid-form medication elements 201. An example of the former can include a medication pellet and an example of the latter a liquid filled capsule. In preferred embodiments doses 200d comprise solid form medication elements 201 configured to dissolve in brain tissue and/or cerebrospinal fluid found bathing the brain. According to one or more embodiments store 140 corresponds to a belt 140 to which doses 200d may be attached. In such embodiments, device 130 may include a mechanism 150 (also referred to herein as transfer mechanism 150) for engaging belt 140 and transferring an individual dose 200d of medication 200 from the belt through port 135 to deliver it to a selected tissue delivery site DS and then advance the belt for the delivery of the next dose 200d of medication 200. In alternative embodiments, a separate mechanism/drive source (not shown) may be used for advancing belt 140.

According to many embodiments, mechanism 150 includes an advancement member 151 configured to advance medication element 201 from within the housing 131, through catheter 120 to delivery site DS. According to one or more embodiments, member 151 corresponds to a metal stylet which may comprise various shape memory metals (e.g., NITONOL, stainless steel) allowing the member 151 to be wound or otherwise contained in housing 131 in a non-linear shape and then be unwound to a linear shape. Member 151 is also desirably configured to bend and flex (and have other pushability characteristics known in the guide wire art) so as to be advanced through and negotiate the curves in catheter 120 in going from port 135 to the tissue site TS in the brain. Member 151 has may be driven by an electric motor (e.g., a linear induction motor) or other drive means known in the art electric. In particular embodiments, it may be driven by rollers 150r integral to otherwise driven by an electric motor. Also, it may have a shaped distal tip 152 such as ball shape to advance element 201 through lumen 123. The distal tip 152 may also have other shapes such as a hot dog shape or a concave shape having a concavity sized to engage the diameter of a dose 200d. The distal tip 152 may also be configured to sense contact with the dose 200d so as to be able to determine that the dose 200d is being advanced and that the dose 200d has been ejected. For example, the distal tip 152 and/or the member 151 may be capacitively coupled to the dose 200d so as to sense changes in capacitance when the tip 152 makes and breaks contact with the dose 200d. Doses 200d are typically individual packaged in packaging 141 (also referred to herein as packaging containers 141) which may integral with or otherwise attached to belt 140. Accordingly, in such embodiments, mechanism 150 and member 151 may further be configured to puncture packaging container 141 and push out dose 200d. Various embodiment of the invention also contemplate other means for advancing medication element 201 through lumen 123 to delivery site DS. Such means may include, for example, pneumatic, hydraulic or magnetic drive means.

Packaging containers 141 may comprise various foil packaging known in the pharmaceutical arts and according to preferred embodiments are substantially impermeable to air and water vapor. In use such embodiments allow for the long term storage (e.g., years) of dose 200d in device 130. In some embodiments, multiple doses 200d (e.g., 2, 3, 4 or even more doses) of medication 200 may be packaged in an individual packaging container 141. Such doses may include the same or different drugs 210 allowing for the treatment of the same or multiple conditions. According to one more embodiments having multiple doses 200d in the same container 141, the container can include a first dose of drug 210 configured to rapidly dissolve in brain tissue to acutely treat an epileptic seizure or other neurologic condition (e.g., a migraine) and a second dose configured to more slowly dissolve so as to provide for a long maintenance dose to prevent the re-occurrence of the seizure or other condition.

In many embodiments, port 135 comprises a sealable septum 136 allowing a solid dose of medication 200 to be passed through the septum by mechanism 150 without the ingress of fluids into housing interior 133. Septum 136 can comprise various elastomeric polymers such as silicone or polyurethane which have sufficient resilience to open and then seal itself after being punctured or otherwise opened by the passage of medication element 201 such as a medication pellet.

As is described above, medication 200 typically comprises one or more drugs or other therapeutic agents 210 for the treatment of one or more conditions such as various neurological conditions described herein. Medication 200 may also include one or more pharmaceutical excipients 220 including for example, one or more of disintegrants, superdisintegrants, binders, anti-oxidants and other excipients known in the art. Desirably, the one more excipients including are selected to be non-pyrogenic and otherwise inert with brain tissue. When in solid form medication elements may 201 correspond to tablets or pellets, with other shapes also contemplated (e.g., spheres). According to one more embodiments, when in solid form, medication elements 201 are configured to dissolve in brain tissue and/or in cerebral spinal fluid within the ventricles in brain to release drug 210. In particular preferred embodiments medication elements 201 are configured to rapidly dissolve in brain tissue and/or CSF so to acutely treat or prevent an epileptic seizure or other acute neurologic condition. In such embodiments, medication elements 201 may comprise various super disintengrants known in the art including super disintengrants which rapidly dissolve in CSF. Also in such embodiments, solid form medication element 201 may have a porous structure configured for rapid ingress of CSF into the interior space of the element. In particular embodiments, the dose of the selected drug 210 (e.g., furosemide or other loop diuretic) can be titrated based on a measurement of the volume of all or a portion of the patient brain. Such measurement may be made by MRI other medical imaging method known in the art. The particular volumes measured can include the total volume of the brain as well as the volume of space in the ventricles. The later measurement providing an indication of the volume of CSF within the brain which in turn allows for the achievement of a selected concentration of drug in the CSF. In use, such embodiment allow for delivery of a dosage of drug to the patient to more precisely achieve obtain a desired therapeutic index for a given drug. This in turn, results in a more efficacious clinical effect (e.g., blocking of ion pump co-transporters causing cortical spreading depression) while minimizing adverse side effects (e.g., adverse peripheral effects such as electrolyte loss, excess diuresis, etc.)

Figure 19:
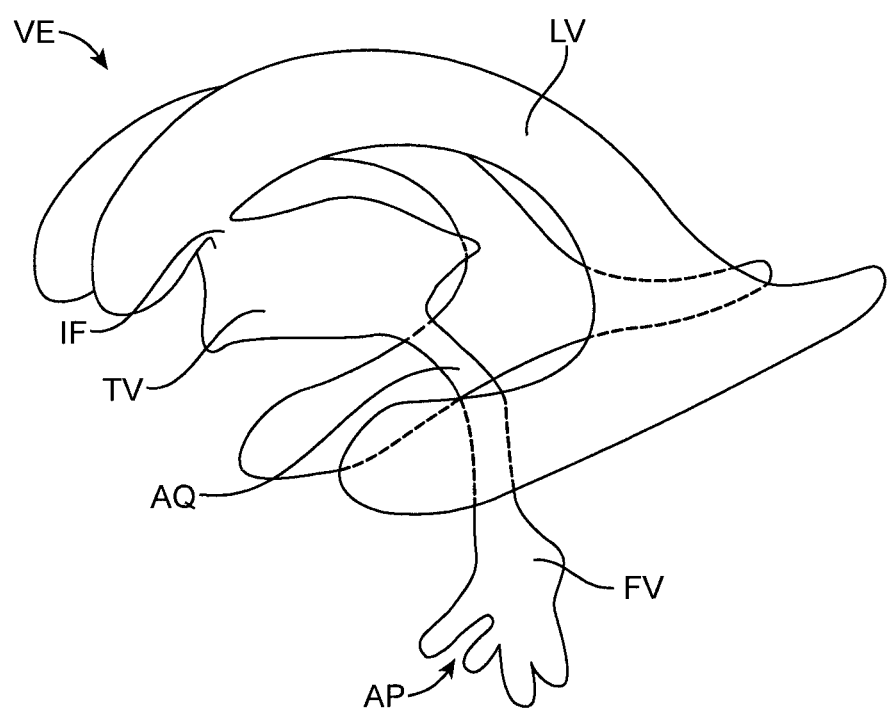
FIG. 19 is a perspective view of the ventricular system of the brain.

Device Positioning in and Delivery of Medication to the Ventricles in the Brain: In many embodiment, drug delivery system 105 is configured to deliver a drug pellet or other solid form medication element to the ventricles of the brain. Accordingly, a brief discussion of the anatomy of the brain and ventricles will be presented. The ventricles VE of the brain are shown in FIG. 19. The lining of the ventricular system of the brain is known as the ependymal. Cerebrospinal fluid (CSF) is produced by the choroid plexus which consists of modified ependymal cells. The majority of CSF is produced by the lateral and 3rd ventricle choroid plexus. Flow of CSF is from the lateral ventricle LV through the interventricular foramen IF to the third ventricle TV through the aqueduct AQ to the fourth ventricle FV and finally through the lateral and median aperture AP providing circulation to the subarachnoid space and spinal cord.

CSF is produced at a rate of approximately 20.8 ml/hr. CSF volume is recycled approximately four times daily. Intracranial pressure (ICP) typically equals CSF pressure in the ventricle when measured in a horizontal patient. Such pressure is normally in a range of about 7 to 15 mmHg. Pressures above 20 mmHg, which correspond to approx. 0.38 psi, are considered abnormal. Therefore it may be desirable that the catheter, including the diffusion chamber, flex when greater exposed to pressures greater than about 20 mmHg (and more preferably greater than about 15 mmHg) is applied so as not to deform the ventricle. Therefore, according to some embodiments, it may be desirable that the catheter including the diffusion chamber have sufficient flexibility to exert no more than about 20 mmHg of pressure/force to ventricular walls of the brain when the catheter is advanced or otherwise positioned in the ventricles of the brain.

Focal deformation of brain anatomy can also cause adverse physiological and/or neurological effects. Symptoms could include behavioral changes, decreased consciousness, headaches, lethargy, weakness, numbness, vision problems, seizures, vomiting and changes in heart rate and respiration rate. It has been reported that such symptoms can occur above 3 mm of deformation. Therefore, according to some embodiments, it is desirable that the catheter including the diffusion chamber have sufficient flexibility to cause no more than about 3 mm of deformation of the ventricular wall when being advanced or position in the ventricles of the brain.

Referring now to FIGS. 2b and 16a-e, a method of introducing introducer 20 and deploying electrode members 30 will now be discussed. Prior to introduction of apparatus 10, a patient having epilepsy or other condition characterized by ANEA can undergo a series of EEGs or other related brain scans to determine the location and other characteristics of a foci of ANBNEA likely causing the condition to be treated (similar method may also be used for determining origins of cortical spreading depression). This information can then be used to determine the target tissue site TS for deployment of the electrode members and thus the corresponding site in the skull for the introduction of the introducer. In many cases, the introducer can be introduced through a burr hole plug; however, it will be appreciated this is exemplary and that other approaches are equally applicable. After the burr hole BH has been drilled and burr hole plug 61 is positioned, the introducer is advanced into brain tissue to the desired target tissue site TS. The advancement can be done under fluoroscopic or other form of medical imaging observation. Positioning of the distal tip 22 of the introducer at the desired target site TS can be facilitated by the use of a distal tip marker on the introducer. Additionally, the introducer can include graduation markings 24 along its length indicating the depth of insertion. Once inserted the desired depth, the surgeon can then lock the introducer in place using locking device 62. Determination that the introducer has been locked in place can be achieved through a signal sent by, for example, contact sensor 63.

Electrode members 30 can then be deployed to achieve a detection volume DV having a selectable size and shape. The electrode members 30 can be deployed individually, or collectively. They can also be advanced by hand or using an advancement member 28 (coupled to the proximal portions of the members 30) or by other advancement means known in the art. The depth of insertion of the electrode members can be controlled by, for example, using a stop placed on advancement member 30 (not shown) and/or by means of a stop 37 (FIG. 3) placed on each electrode member 30. Deployment of members 30 can also be guided by fluoroscopic observation or other imaging modality. In some embodiments, this process can be facilitated by superimposing onto the fluoroscopic image (or other image) a marker or other indicia denoting the likely location of the foci F of ANEA. This physician can use this marker to locate and orient the position of the deployed electrode members so as to optimize the detection of ANEA signals from Foci F. For example, the physician can use the marker to deploy the electrode members such that their distal ends are placed within a selectable distance of Foci F. Also, it can be used to achieve a selectable angular orientation, e.g., 90°, with the longitudinal axis of one or more of the electrode members so as to maximize the voltage produced at those electrode members from an electric field vector generated by ANEA signals from foci F.

After deployment of the electrode members, the physician can perform one or more tests to ascertain that the electrode members are functioning and capable of detecting ANEA signals from one or more foci F. This can include sending a test signal from a separate electrode (not shown) positioned in the brain so as to have the same directional orientation with respect to the electrode members as Foci F does. The test signal can be configured to simulate the amplitude and frequency of an actual ANEA signal. If the electrode members are not able to detect the test signal, the physician can redeploy all or a portion of the electrode members until he or she gets the desired response. In particular embodiments, the test signal can not only be used to test the functionality of the deployed electrode members, but also as a beacon to assist in their deployment. In such embodiments, the physician can deploy and position the electrode members while the test/beacon signal is being sent so as to maximize the resulting voltages measured by the electrode members. After the electrode members 30 are correctly deployed, the electrode members can be locked in place using locking device 63 or another locking mechanism. The burr plug will then be sealed/closed using standard methods known in the art and connectors 40 (FIG. 6a) can be connected to control module 80 (or other like device) via one more wires or the connection can be wirelessly. The control module 80 can be implanted subcutaneously in the head and neck area or can be worn by the patient. In embodiments where module 80 contains a drug delivery device 90 for treating the foci F of ANEA, the module 80 will typically be implanted subcutaneously in the head and neck area. In embodiments where it does not, it can positioned in any number of location or can be worn by the patient. In such embodiments, a separate drug reservoir and drug delivery device (which may be substantially the same or different as device 90) can be implanted in the head and neck so as to provide for intracranial delivery of the drug. Alternatively, the drug can be delivered intravenously (IV) in which case the reservoir and drug delivery device can be positioned at any number of locations and/or externally worn by the patient. In embodiments where a combination of intracranial and IV delivery are used, a drug reservoir/delivery device can be implanted in the head and neck areas and another delivery device/reservoir can be worn by the patient for IV delivery.

Figure 17A:
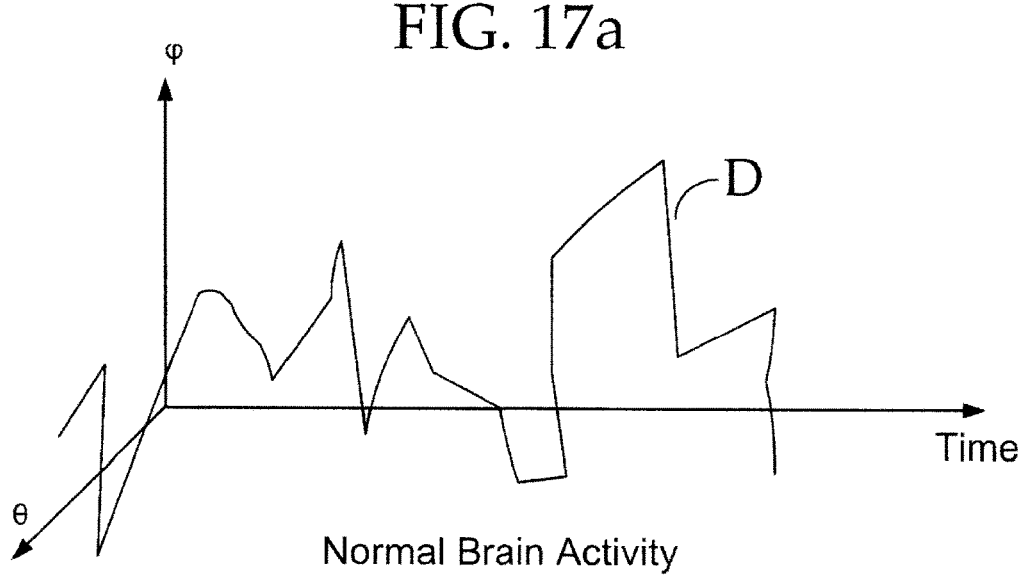
FIGS. 17a and 17b are 3d plots of the direction of an electric field vector over time in the brain.
Figure 17B:
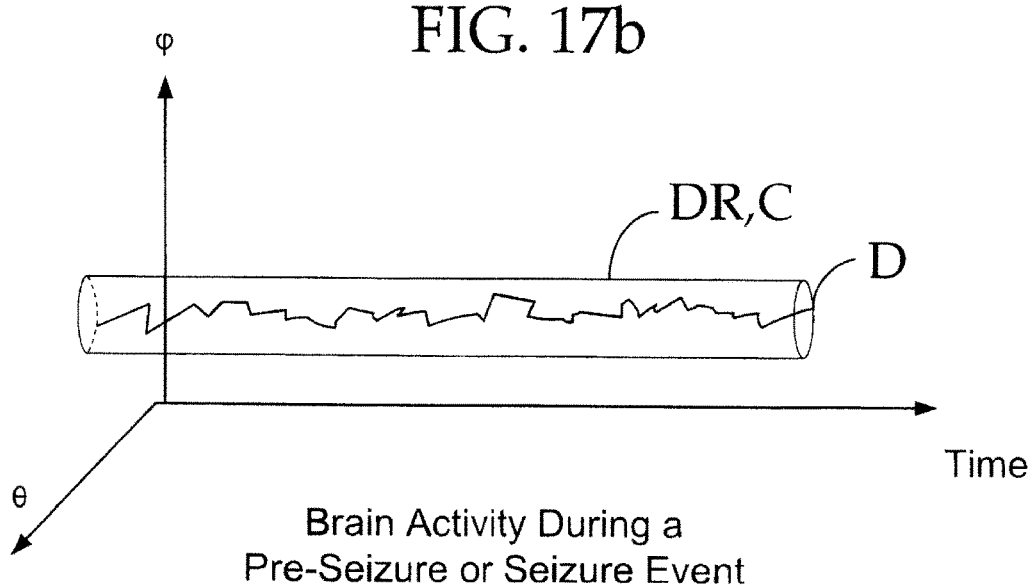
Figure 18:
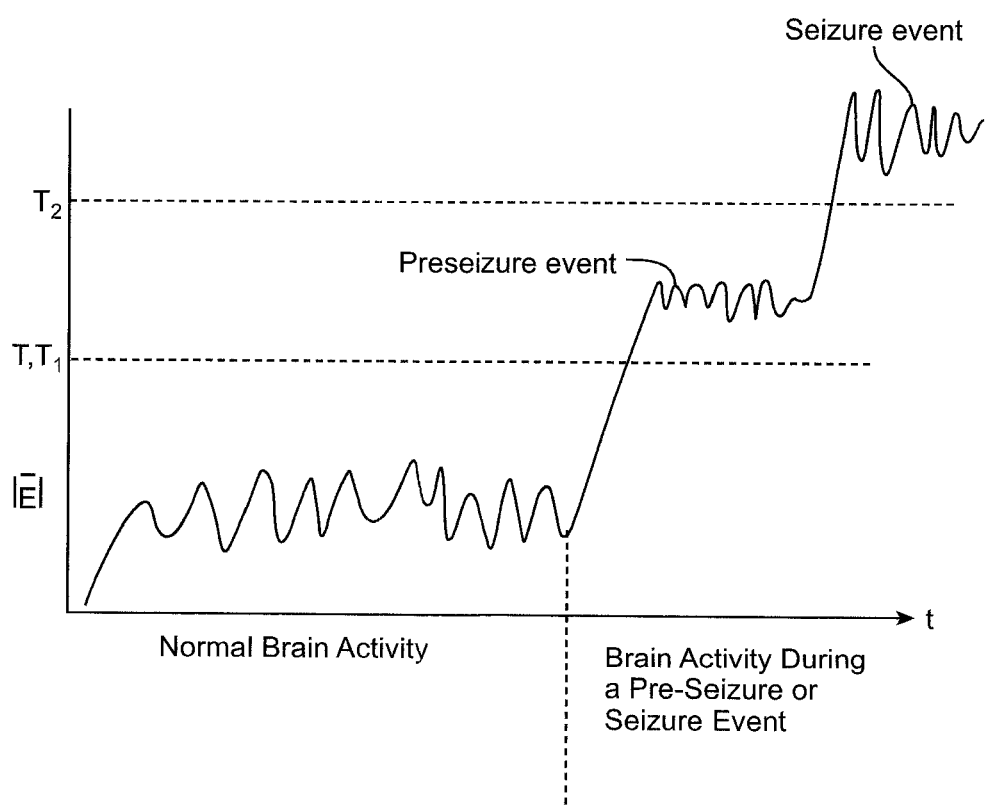
FIG. 18 is plot of the amplitude of an electric field vector over time during periods of normal and aberrant neural-electric activity in the brain.

A discussion will be presented of methods of detecting ANEA using apparatus 10 and utilizing this information, to detect a neurological event or condition such as a seizure. In these and related embodiments, methods will be presented for detecting both a pre-seizure event and a seizure event (such events can correspond to pre-seizure and seizure states). For ease of discussion, the pre-seizure and seizure events will refer to an epileptic pre-seizure event (also as a pre-ictal state or event) and epileptic seizure event (hereinafter seizure); however, it will be appreciated that these methods are applicable to detecting pre-seizures events/states and seizures associated with other neurological events or conditions and syndromes such as migraines headaches and other related conditions. As discussed above, apparatus 10 measures electric field vectors in the brain generated by neural activity by measuring the voltage differential between each electrode member 30 and the reference electrode 35 and using these values to calculate electric field vector $\overline{E}$. Various characteristics of field vector $\overline{E}$ can then be used as an indicator of a seizure or pre-seizure event. Referring now to FIGS. 17-18, during normal brain activity, the electric field vector $\overline{E}$ will typically have a random direction D (as defined by angles $\varphi$ and $\theta$ described above) as is shown in FIG. 17a. Also during normal activity, the magnitude/amplitude |$\overline{E}$| of the electric field vector will be random but will have a time average value which stays below a particular threshold T as is shown in FIG. 18. In contrast, during a period of aberrant neural-electric activity such as that occurring during a pre-ictal event or a seizure event, electric field vector |$\overline{E}$| will dwell in a particular direction D or directional region DR for an extended period of time compared to normal brain activity as is shown in FIG. 17b. The dwell time can be tenths of a second to several seconds or longer (e.g., 0.10 to 10 seconds with specific embodiments of 0.2, 0.5, 1, 2, and 5 seconds) shorter dwell times are also contemplated (e.g., 0.01 to 0.1 seconds). During a pre-seizure or seizure event, the directional region DR will be bounded by a cylinder C or related geometric shape. Also, the electric field amplitude will exceed a threshold T above normal activity for a sustained period of time as is shown in FIG. 18. This can include exceeding a first threshold $T_1$, for a pre-seizure or other like event and a second threshold $T_2$, for a seizure or other like event.

In particular embodiments, algorithms 83 resident within module 80 can use one or more of the above changes in electric field vector characteristics (e.g., in amplitude and direction of the field vector) to detect a period of ANEA indicative of a pre-ictal event, epileptic seizure, a wave of cortical spreading other seizure or neurologic event or(such periods of ANEA can thus be used as a marker of a pre-ictal event, epileptic seizure cortical spreading depression or other seizure or neurologic event). For example, a pre-ictal event or seizure may be detected based on the electric field vector staying in a particular direction or directional cone for longer than a selected period of time. For applications where the location of a known foci of ANEA has previously been determined prior to placement of apparatus 10, additional algorithmic weightings can be employed if the direction of the detected electric field vector is within a selected directional cone that includes the direction of the previously detected Foci F (this direction being the direction of the foci relative to distal end of the introducer).

In another example of a predictive electric field vector characteristic, a pre-ictal event or seizure may also be detected based on whether the electric field amplitude exceeds a particular threshold and more preferably, whether the time average of the electric field amplitude exceeds the threshold. A combination of these two approaches can also be used so that the direction and amplitude of the electric field vector both need to exceed threshold values. Additionally, pattern recognition algorithms can be employed to detect particular signal patterns in the electric field which are indicative of a pre-ictal event or seizure (also known as a seizure event). A data base of such patterns can be generated from EEG measurements taken from the patient themselves, an epileptic patient population or a combination of both. Again, the detection algorithm can employ both pattern detection with one or both of electric field amplitude and direction so to make a determination of pre-ictal event or seizure. A detection score exceeding a certain threshold can be used to predict a pre-ictal event or seizure, with a score over a first value indicative of value pre-ictal event and a score over a second value indicative of a seizure. Also, weightings can be assigned to these or other detection parameters so that algorithm generates a detection score value as a function of these parameters. Weightings can be chosen from a weighting database taken from a patient population or they can be established for each individual patient by monitoring the patient over a period of time using external EEG electrodes or with apparatus 10 in place and then inducing a pre-seizure or mild epileptic seizure and recording the data for the these detection parameters. The weightings can also be updated after subsequent pre-ictal events or seizure either manually by a health care provider or by algorithm itself using self learning methodology.

When the detection score exceeds a threshold value indicative of a pre-ictal event or seizure event, module 80 can perform one or more functions. First, now referring to FIG. 14, the module can send a signal 85 to an alarm 120 to alert the patient so that they can take precautionary measures such as taking medication as well as sitting or lying down or discontinuing any hazardous activities. It can also send a wireless signal 86 (via a RF or IR port to a monitoring device 130 in a hospital or doctor's office (this can be achieved using a cellular phone or various medical telemetry devices known in the art). It can also send a signal 87 to a drug delivery device 90 to deliver a dose of an anti-seizure medication (e.g., a solid dose of a loop diuretic such as furosemide) and/or a signal 88 to a stimulating device 100 to send an inhibitor signal 101 via electrode members 30 (or other implanted electrode) to prevent the onset of a seizure or stop an occurring seizure. In various embodiments a combination of both interventions can be used Inhibitory signal 101 can have various forms. In one embodiment, it can be configured to depolarize the regions of the around the Foci F causing the pre-ictal event or seizure. In other embodiments, it can be matched to the particular pattern of aberrant neural-electric activity causing the pre-ictal event or seizure so as to be out of phase with the aberrant neural-electric activity or otherwise dampen its effect on surrounding tissue. In preferred embodiments, the inhibitory signal is delivered using electrode members 30 as stimulating electrodes 36; however, the use of separate electrodes as stimulating electrodes is also contemplated.

For embodiments employing drug intervention, the delivered dose of drug can be titrated based upon the value of the detection score and/or whether the detected event is a pre-ictal event or a seizure. A baseline dosage can be determined based upon various patient parameters, such as weight, age, type of epilepsy (e.g., partial-onset seizure) and severity of seizures. Suitable anti-seizure medications can include phenytoin sodium (Dilantin), ion transporter agonists such as thiazides and thiazide-like diuretics, and cation chloride ion transport agonists such as furosemide, and furosemide like diuretics as well as the chemical analogues and derivatives of each. In preferred embodiments, the anti-seizure compound corresponds to furosemide including its solid form. Still other anti-seizure medications known in the art also contemplated. During and after drug delivery, system 10 can be configured to continue to monitor brain activity to determine if the pre-ictal event or a seizure has subsided and to what degree. Repeat dosages of drug can be administered as needed depending upon the detection score or other factor. Increased dosages can be given if the detection score remains above a selected level. Also, selectable dosing regimens can be used depending upon one or more of the detection score, type of epilepsy, pattern of seizures, age, weight, etc. For example, for a pre-ictal event, a bolus dose could be given intracranially (e.g., a dose of furosemide or other loop diuretic and/or ion co-transporter antagonist), whereas for a full seizure, treatment could include an intracranial bolus or initial dose (e.g., a loop diuretic, and/or ion-transporter antagonist) followed by a second dose which may be administered over a longer term than the first dose (e.g., a period of minutes or hours). The second dose may be the same or a different drug and may be administered intra-cranially or by another administration route such as intravenous. For embodiments where the same drug is used for both doses, the second or maintenance dose may be the same or set percentage of the first does, for example, 50, 25 or 10% by weight (or other parameter) of the first dose. Also in various embodiments, a selectable dosing regimen can be delivered based not only on a individual detection score, but also based on a time pattern of detection scores, even if the scores are below a pre-ictal event or seizure event threshold. For example, a dose of drug could be delivered based upon a certain number of spikes in the detection score over a selected period of time. Various dosing regimens can also be configured to use a combination of intracranial and IV administration using an intracranial delivery device and an IV pump.

In various embodiments, the dosing regimen can be tailored to the particular drug or combination of drugs delivered. For use of furosemide or other like drug, the dosing regimen can be in the form of an initial or bolus dose configured to achieve a selected peak intracranial concentration and/or therapeutic effect (e.g., prevention or slowing of cortical spreading depression) with a subsequent maintenance dose or doses of the same or a different drug to prevent the re-occurrence of cortical wave depression. In particular embodiments including use of multiple seizure drugs, the detection score can also be used to determine what drugs are actually given. For example, a detection score above a first threshold can be used for a first drug and another detection score above a second threshold can be used to select a second drug.

In various other embodiments of methods for detecting aberrant neural-electric activity causing a seizure or pre-seizure event (and/or cortical spreading depression associated with it), changes in tissue impedance can also be used with such changes being measured by electrode members 30. Such approaches operate on the principle that the impedance of brain tissue changes during a pre-seizure or seizure state. Tissue impedance can be measured by applying a slight voltage or current between conductive portion 34 (FIG. 6*b*) and reference electrode 35. Both real and the imaginary component of impedances can be used. Similar to methods employing voltage/electric field vector measurements, measured impedances can be used to generate detection score as mean do predict both pre-seizure and seizures events. In particular embodiments, impedance measurements can be combined with voltage/electric field vector measurements to further improve the sensitivity for predicting both pre-seizure and seizures events.

Cortical Spreading Depression: Cortical Spreading depression (CSD) is a propagating wave of transient neuronal hyperexcitability followed by a period of electrical silence. This wave of excitation-inhibition moves slowly (~3-5 mm/min) across cortical and other areas of the brain. CSD involves a massive redistribution of ions (e.g., $K^+$, $Na^+$, $Ca^{2+}$, $Cl^-$) between intracellular and extracellular compartments. Glial cells are intimately involved in these ionic fluxes. Therefore, ion pumps (specifically Na+—K+−2Cl— (also described as NKCCl) co-transporters) on glial cells are implicated in CSD. These pumps utilize ion-dependent transporters. Accordingly, various embodiments of the invention contemplate use of ion ion-dependent transporters agonist (e.g., furosemide or other loop diuretic) to block or slow the ion fluxes responsible for cortical spreading depression associated with a neurological epileptic pre-seizure or other adverse neurological event or condition such as migraine headache.

Treatment of Cortical Spreading Depression and Epilepsy Using Furosemide: Furosemide I (available under the trade name LASIX) is a well established loop diuretic used to treat fluid retention and high blood pressure. Loop diuretics are a class of drugs which act on the ascending loop of Henle in the kidney. Specifically they block a co-transporter (known as The Na—K—Cl co-transporter or NKCC, SLC12A2) resulting in reduced reabsorption of NaCl and Potassium in the nephron, in turn resulting increase diuresis i.e., urine production. They are primarily used in medicine to treat hypertension and edema. Furosemide both in epileptic animal models as well as in human patients has been shown to block evoked and spontaneous epileptic neural activity and subsequent cortical spreading depression by blocking a similar ion-transporter in the brain. However, furosemide has a number of adverse side effects including, for example, electrolyte loss/imbalance, hyperglycemia, otoxicity, hyperuricemia and resulting gout, and low potassium levels as well as increased diuresis to name a few. If the drug were to be given orally and/or intravenously in concentrations sufficient for the prevention of epilepsy one or more of these side effects would occur, precluding its use and/or significantly limiting its applications. Patients would also have to be regularly monitored for one or more of these conditions including electrolyte loss (e.g., loss of electrolytes such as Na, K, Cl, Ca. Mg, etc.). Further, for acute situations (e.g., the onset of a seizure), oral administration would not be fast enough as the drug may take 30 minutes or longer to get into the patient's blood stream, if they were even able to take the drug at the onset of the seizure due to the loss of motor control which occurs at the onset of the seizure. IV administration would also be impractical as well since the patient may not be able to inject themselves fast enough after the seizure began (even if they carried around an syringe of the solution), particularly since they quickly loose motor control at the onset of the seizure.

Various embodiment of the invention overcome these problems by providing apparatus, systems and methods for the treatment and prevention of epilepsy (and other conditions associated with CSD such as migraine headache) by the use of intracranial delivery of furosemide (and/or its analogues and derivatives) so that drug is delivered directly to the patient's brain. Further because the drug is delivered directly to the brain, the dose used to treat and/or prevent the epileptic seizure can be substantially less than would cause any appreciable undesirable peripheral effects, such as increased diuresis, electrolyte loss, hyperglycemia, etc. as is explained in further detail herein. In many embodiments, the delivery of furosemide and/or its analogues and derivatives is done intra-cranially using for example various embodiments of a drug delivery apparatus described herein. This apparatus may comprise a drug storage chamber coupled to an intracranial catheter that is inserted and positioned in the patient's brain tissue (including for example, deep brain tissue) through a burr hole or other opening made in the patient's brain tissue with an adaptive fitting positioned in the burr hole allowing for the long term placement of the catheter in the brain. In preferred embodiments, the apparatus can be configured for the delivery of a solid medication into the brain, so as reduce the risk of any pathogens (which are more likely to be present in liquid form) while allowing for the long-term storage of a multi-year supply of doses of furosemide in the storage chamber which may be subcutaneously implanted at the base of the skull for rapid advancement of the solid drug into the brain. In addition to the delivery of furosemide for the treatment of epilepsy or other condition associated with CSD, various embodiments of the invention also contemplate other loop diuretics, for the treatment of CSD associated conditions including for example, bumetanide, ethacrynic acid and torsemide.

In various embodiments, the dosage of furosemide (or other loop diuretic) is selected to produce a localized effect in the brain for seizure prevention, while minimizing peripheral effects, in particular effects on the kidneys causing diuresis and electrolyte loss. Desirably, the dosages of furosemide (and related analogues and derivative) are at least ten fold below the threshold dosage which produces a significant increase in diuresis and/or significant decrease in the patient's electrolyte level(s) (e.g., sodium, potassium). As used herein, a significant increase in diuresis is more than about a 10% increase in the patient's urine production (more preferably more than about a 5% increase), which may correspond to either a rate of urine production or total output over a period of time (e.g., one hour, two hours, 12 hours etc.). Also, as used herein, a significant decrease in an electrolyte is more than about a 5% decrease a patient's plasma concentration of an electrolyte, for example, potassium or sodium concentration. Still smaller decreases are also contemplated such as decrease of more than about 2.5% or even 1%. Also, deceases of other electrolytes are also contemplated as well, for example, calcium, magnesium, hydrogen phosphate, and hydrogen carbonate. Also, decreases in the patient's electrolyte level in other areas and/or tissues of the body are also contemplated such as decrease in their electrolyte level(s) in their interstitial fluid, intracellular fluid, muscle tissue, heart tissue, pancreatic tissue and other areas as well.

The aforementioned threshold dose(s) of furosemide for many patients is approximately, 20 mg. However, that threshold may be adjusted based on or more of a patient's, weight, age and medical condition (e.g., epilepsy, type of epileptic seizure, frequency of seizures, etc.). Various dose response curves and urine output measurement methods may be used to determine the specific threshold dose in a given patient, patient population (e.g., women with epileptic seizures) or subpopulation (women between 40-50 with grand mal seizures). Thresholds may also be determined using correlations to thresholds determined by such methods in one or more animal models (e.g., a rat, monkey, pig, etc.). Accordingly, in various embodiments, the therapeutically effective dosage of furosemide (and/or its analogues and derivatives) delivered to the brain of the patient can be in the range of can be in the range of about 1 to 2000 μg, about 200-800 μg, about 1 to 1000 μg, about 1 to 10 μg, about 5 to 50 μg, about 10 to 100 μg, about 10 to 500 μg, about 10 to 250 μg, about 20 to 250 μg, about 10 to 100 μg, about 25 to 100 μg, with still other ranges contemplated. In particular embodiments, the dosage of furosemide or other loop diuretic can be titrated based upon a measurement of the ventricle volume in the patient's brain (e.g., by MRI) so as to produce a selected concentration of drug in the CSF fluid in that volume. Further in various embodiments, one or more of the previous dosages of furosemide (and/or its analogues and derivatives) can be delivered intra-cranially, using for example, one or more embodiments of drug delivery systems and apparatus described herein such for example a system 105 and drug delivery device 95 and/or 115.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, various embodiments can be sized or otherwise adapted for various pediatric applications or the treatment of any number of neurological event or conditions involving aberrant neural-electric activity and/or cortical spreading depression.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus for delivery of medication to the ventricles within the brain of a patient, the apparatus comprising:
    a supply of multiple solid form medication elements;
    an advanceable belt configured to store the supply of multiple solid form medication elements;
    a flexible delivery member having a proximal end, a distal end, and a lumen for advancement of a solid form medication element through the delivery member, the solid form medication element comprising at least one drug, wherein the flexible delivery member is configured to be advanced into a selected ventricle of the brain from a site outside the brain;
    a diffusion chamber coupled to the distal end of the delivery member; the diffusion chamber having a wall and an interior volume for receiving the solid form medication element and at least one diffusion section positioned in the wall allowing cerebrospinal fluid (CSF) to enter and exit the chamber;
    an advancement member configured to advance individual solid form medication elements from the supply through the flexible delivery member to the diffusion chamber;
    wherein the chamber is configured to i) retain a solid form medication element received from the delivery member; ii) dissolve the solid form medication element in fluid within the interior volume to form a drug solution; and iii) diffuse drug from the drug solution through the at least one diffusion section to CSF within the selected ventricle of the brain; and
    means for receiving the solid form medication element from the flexible delivery member into the diffusion chamber while preventing CSF mixed with the solid form medication element in the diffusion chamber from exiting into the flexible delivery member; and
    wherein the diffusion chamber and the delivery member have a flexibility configured such that during advancement of the apparatus into the brain, the apparatus conforms to a shape of the selected ventricle.
2. The apparatus of claim 1, wherein the diffusion chamber and the flexible delivery member have a flexibility configured such that during advancement of the apparatus into the brain, the apparatus does not deform a ventricular wall of the brain sufficiently to cause a significant physiological effect to brain.
3. The apparatus of claim 2, wherein the diffusion chamber deforms the ventricular wall no more than about 3 mm.
4. The apparatus of claim 2, wherein the diffusion chamber applies no more that about 20 mmHG of pressure to the ventricular wall.
5. The apparatus of claim 2, wherein the physiologic effect is a decrease in CSF production.
6. The apparatus of claim 2, wherein the physiologic effect comprises at least one of a neurological effect, loss of consciousness, pain or numbness, or change in heart rate.
7. The apparatus of claim 1, wherein the solid form medication element has a pellet shape.
8. The apparatus of claim 1, wherein the solid form medication element comprises a drug for the treatment of epilepsy.
9. The apparatus of claim 8, wherein the drug comprises furosemide.
10. The apparatus of claim 1, wherein the means for preventing CSF mixed with the medication in the diffusion chamber from exiting into the flexible delivery member includes a self-closing slit septum valve positioned at a proximal portion of the chamber, the septum valve configured to open to allow advancement of the solid form medication element into the diffusion chamber and then close to provide a fluidic seal between the diffusion chamber and the flexible delivery member.
11. The apparatus of claim 1, wherein the at least one diffusion section is positioned around a circumference of the wall of the diffusion chamber.
12. The apparatus of claim 1, wherein the at least one diffusion section comprises at least two diffusion sections.
13. The apparatus of claim 12, wherein the at least one diffusion section comprises at least four diffusion sections.
14. The apparatus of claim 13, wherein the at least four diffusion sections are offset by about 90 degrees with respect to a longitudinal axis of the diffusion chamber.
15. The apparatus of claim 1, wherein the at least one diffusion section comprises a permeable membrane.
16. The apparatus of claim 15, wherein the membrane comprises polyimide.
17. The apparatus of claim 15 wherein the diffusion chamber includes a valve for releasing pressure within the diffusion chamber.
18. The apparatus of claim 17, wherein the valve comprises a slit in the wall of the diffusion chamber.
19. The apparatus of claim 1, wherein the diffusion chamber comprises a section of a wall of the diffusion chamber having a plurality of openings for diffusion of CSF in and out of the diffusion chamber.
20. The apparatus of claim 19, wherein the openings comprise slits.
21. The apparatus of claim 20, wherein the slits have a length in a range of about 0.25 mm to about 5 mm.
22. The apparatus of claim 19, wherein the plurality of openings comprise 32 openings.
23. The apparatus of claim 19, wherein the openings have a diameter in a range of about 0.1 mm to about 0.5 mm.
24. The apparatus of claim 1, wherein the diffusion chamber comprises silicone.
25. The apparatus of claim 1, wherein the diffusion chamber is sufficiently flexible to bend up to about 30° when advanced in the ventricles of the brain.

26. The apparatus of claim 1, wherein the diffusion chamber is connected to the delivery member by a necked section allowing the diffusion chamber to bend and flex when advanced into the ventricles of the brain.

27. The apparatus of claim 1, wherein the diffusion chamber wall has a plurality of channels configured for maintaining diffusion of drug from the diffusion section when the diffusion section contacts the ventricle wall.

28. The apparatus of claim 27, wherein the channels continue along a length of the flexible delivery member so as to allow transport of the drug through the channels in a proximal direction of the delivery catheter so as to be delivered into brain tissue.

29. The apparatus of claim 28, wherein the channels have sufficient length so to allow drug solution to be delivered to a surface of the brain.

30. The apparatus of claim 27, wherein the channels correspond to convolutions in the wall of the diffusion chamber.

31. The apparatus of claim 27, wherein the channels correspond to slots in the wall of the diffusion chamber.

32. The apparatus of claim 27, wherein the plurality of channels comprise at least eight channels.

33. A system for the delivery of solid form medication to the ventricles of the brain of a patient, the system comprising: the apparatus of claim 1, and a drug storage device operably coupled to proximal end of the flexible delivery member, the storage device configured to store a plurality of solid form medication elements.

34. An apparatus for delivery of solid form medication to the ventricles within a brain of a patient, the apparatus comprising:
a supply of multiple solid form medication elements;
an advanceable belt configured to store the supply of multiple solid form medication elements;
a flexible delivery member having a proximal end, a distal end, and a lumen for advancement of a solid form medication element comprising at least one drug therethrough, the delivery member being configured to be advanced into a selected ventricle of the brain from a site outside the brain;
a diffusion chamber coupled to the distal end of the delivery member, the diffusion chamber having a wall and an interior volume for receiving and retaining the solid form medication element therein, wherein the wall of the diffusion chamber comprises means for allowing cerebrospinal fluid (CSF) to enter into the interior volume, dissolve at least a portion of the solid form medication element, and exit the interior volume with the at least one drug dissolved therein, and wherein the delivery member and the diffusion chamber have a flexibility configured such that during advancement of the apparatus into the brain, the apparatus conforms to a shape of the selected ventricle;
an advancement member configured to advance individual solid form medication elements from the supply through the flexible delivery member to the diffusion chamber; and
means for preventing CSF mixed with the medication in the diffusion chamber from exiting into the flexible delivery member.

35. The apparatus of claim 1, wherein the diffusion section includes a burp valve configured to open at selected pressure differential between an interior and exterior of the diffusion chamber.

36. An apparatus for delivery of medication to the ventricles within the brain of a patient, the apparatus comprising:
a supply of multiple solid form medication elements;
an advanceable belt configured to store the supply of multiple solid form medication elements;
a flexible delivery member having a proximal end, a distal end, and a lumen for advancement of a solid form medication element through the delivery member, the solid form medication element comprising at least one drug, wherein the delivery member is configured to be advanced into a selected ventricle of the brain from a site outside the brain;
a diffusion chamber coupled to the distal end of the delivery member; the diffusion chamber having a wall and an interior volume for receiving the solid form element and at least one diffusion section positioned in the wall allowing cerebrospinal fluid (CSF) to enter and exit the chamber; wherein the chamber is configured to i) retain a medication element received from the delivery member; ii) dissolve the solid form medication element in fluid within the interior volume to form a drug solution; and iii) diffuse drug from the drug solution through the at least one diffusion section to CSF within the selected ventricle of the brain;
an advancement member configured to advance individual solid form medication elements from the supply through the flexible delivery member to the diffusion chamber;
a self-closing slitted septum configured to open to receive the solid form medication element from the flexible delivery member into the diffusion chamber and then close to provide a fluidic seal between the diffusion chamber and the flexible member to prevent CSF mixed with the medication in the diffusion chamber from exiting into the flexible delivery member; and
wherein the diffusion chamber and the delivery member have a flexibility configured such that during advancement of the apparatus into the brain, the apparatus conforms to a shape of the selected ventricle.

37. The apparatus of claim 36, wherein the diffusion section includes a burp valve configured to open at selected pressure differential between an interior and exterior of the diffusion chamber.

38. The apparatus of claim 1, wherein the advancement member is flexible.

39. The apparatus of claim 1, wherein the advancement member is configured to be advanced and retracted through the flexible delivery member.

40. The apparatus of claim 1, wherein the advancement member is a metal stylet.

41. The apparatus of claim 1, wherein the advancement member is a pusher tube.

* * * * *

UNITED STATES PATENT AND TRADEMARK OFFICE
CERTIFICATE OF CORRECTION

PATENT NO. : 10,507,313 B2
APPLICATION NO. : 13/827468
DATED : December 17, 2019
INVENTOR(S) : Mir Imran et al.

Page 1 of 1

It is certified that error appears in the above-identified patent and that said Letters Patent is hereby corrected as shown below:

On the Title Page

Item (60), Should read:
"Continuation-in-part of application No. 13/301,584"

Signed and Sealed this
Twenty-sixth Day of May, 2020

Andrei Iancu
*Director of the United States Patent and Trademark Office*